(12) United States Patent
Umana et al.

(10) Patent No.: US 11,340,234 B2
(45) Date of Patent: May 24, 2022

(54) METHOD FOR THE DETERMINATION OF ANTI-DRUG ANTIBODIES AGAINST AN EFFECTOR FUNCTION SUPPRESSED HUMAN OR HUMANIZED DRUG ANTIBODY

(71) Applicant: Hoffmann-La Roche Inc., Little Falls, NJ (US)

(72) Inventors: Pablo Umana, Wollerau (CH); Uwe Wessels, Penzberg (DE); Kay-Gunnar Stubenrauch, Penzberg (DE)

(*) Notice: Subject to any disclaimer, the term of this patent is extended or adjusted under 35 U.S.C. 154(b) by 352 days.

(21) Appl. No.: 15/587,730

(22) Filed: May 5, 2017

(65) Prior Publication Data

US 2017/0343560 A1 Nov. 30, 2017

Related U.S. Application Data

(63) Continuation of application No. PCT/EP2015/074495, filed on Oct. 22, 2015.

(30) Foreign Application Priority Data

Nov. 5, 2014 (EP) .................................. 14191806

(51) Int. Cl.
*G01N 31/00* (2006.01)
*G01N 33/53* (2006.01)
*G01N 33/68* (2006.01)
*G01N 33/50* (2006.01)

(52) U.S. Cl.
CPC ..... *G01N 33/6854* (2013.01); *G01N 33/5008* (2013.01); *G01N 33/5306* (2013.01)

(58) Field of Classification Search
None
See application file for complete search history.

(56) References Cited

U.S. PATENT DOCUMENTS

| | | | |
|---|---|---|---|
| 5,219,730 A | 6/1993 | Potocnjak et al. | |
| 9,822,181 B2* | 11/2017 | Bonvini | C07K 16/2866 |
| 2009/0286258 A1* | 11/2009 | Kaur | G01N 33/6854 |
| | | | 435/7.1 |
| 2012/0321626 A1* | 12/2012 | Zhou | C07K 16/30 |
| | | | 424/136.1 |

FOREIGN PATENT DOCUMENTS

| | | |
|---|---|---|
| CN | 10288443 A | 1/2013 |
| CN | 103460048 | 12/2013 |
| EP | 0 139 389 | 2/1985 |
| EP | 0 170 302 | 5/1986 |
| EP | 0 962 771 A1 | 8/1999 |
| EP | 0 65 1761 B1 | 9/2002 |
| EP | 1 917 854 | 7/2008 |
| EP | 2 351 792 A1 | 3/2011 |
| EP | 2 354 792 A1 | 8/2011 |
| EP | 2 492 689 A1 | 8/2012 |
| JP | 2011-506943 | 3/2011 |
| JP | 2013-527444 | 6/2013 |
| JP | 2014-514287 | 6/2014 |
| WO | 1987/002778 | 5/1987 |
| WO | 2009/077127 A1 | 6/2009 |
| WO | 2011/057120 | 5/2011 |
| WO | 2011/135024 A1 | 11/2011 |
| WO | 2012/130831 A1 | 10/2012 |

OTHER PUBLICATIONS

Berkova et al., "Development of an Enzyme Immunoassay for the Measurement of Human Tumour Necrosis Factor-x (hTNF-x) Using Bispecific Antibodies to hTNF-x and Horseradish Peroxidase" Biotechnology and Applied Biochemistry 23(2):163-171 (Apr. 1, 1996).
Chen et al., "Rapid Detection of Hepatitis B Virus Surface Antigen by an Agglutination Assay Meiated by a Bispecific Diabody Againt Both Human Erythrocytes and Hepatitis B Virus Surface Antigen" Clinical and Vaccine Immunology 14(6):720-725 (Apr. 18, 2007).
Doppalapudi et al., "Chemical Generation of Bisspecific Antibodies" PNAS 107(52):22611-22616 (Dec. 28, 2010).
ISR for PCT/EP2015/074495.
Porter et al., "An Electro-Active System of Immuno-Assay (EASI Assay) Utilising Self Assembled monolayer Modified Electrodes" Biosensors & Bioelectronics 16(9-12):875-885 (Dec. 1, 2001).
Reinartz et al., "Bispecific Multivalent Antibody Studies by Real-Time Interaction Analysis for the Development of an Antigen-Inhibittion Enzyme-Linked Immunosorbent Assay" Annlyst 121(6):767-771 (Jun 1, 1996).
Wadhwa et al., "Strategies for detection, measurement and characterization of unwanted antibodies induced by therapeutic biologicals" J. Immunol. Methods 278:1-17 ( 2003).
Glick, B. et al. Molecular biotechnology Moscow:Mir,: 182-187 ( 2002).

* cited by examiner

*Primary Examiner* — Lisa V Cook

(74) *Attorney, Agent, or Firm* — Jonathan P. Aumais

(57) ABSTRACT

Herein is reported an anti-drug antibody immunoassay for the determination of the presence of an anti-drug antibody against an effector function suppressed human or humanized drug antibody in a sample comprising the incubation of a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and the determination of the formed complex by the detectable label.

19 Claims, 11 Drawing Sheets

Specification includes a Sequence Listing.

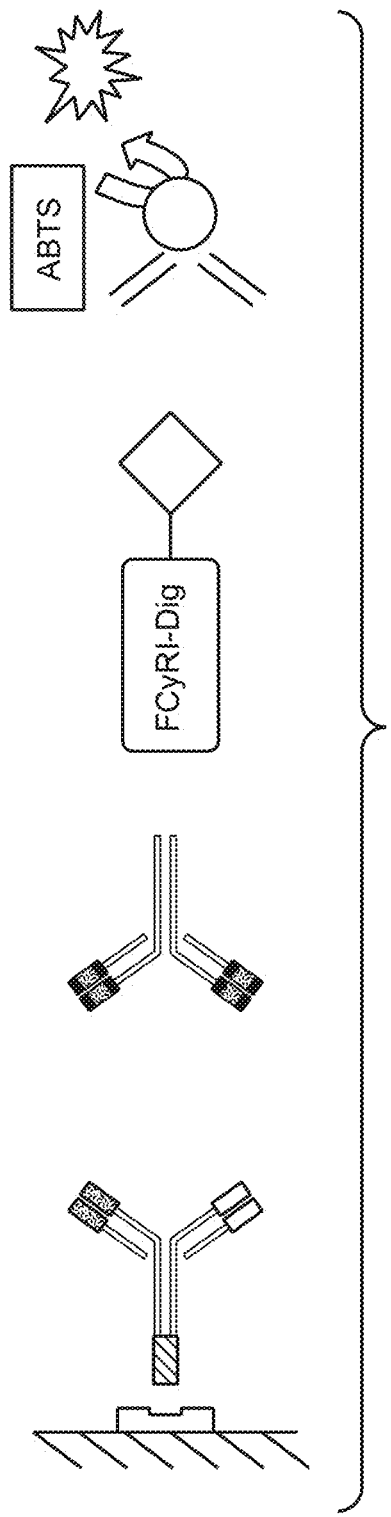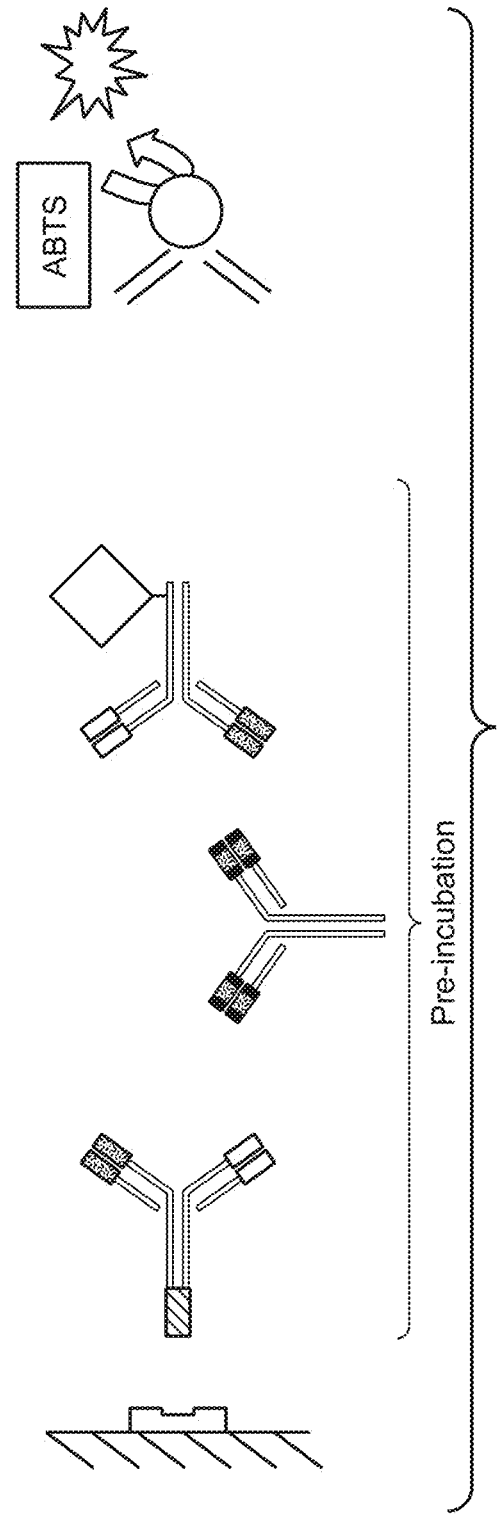

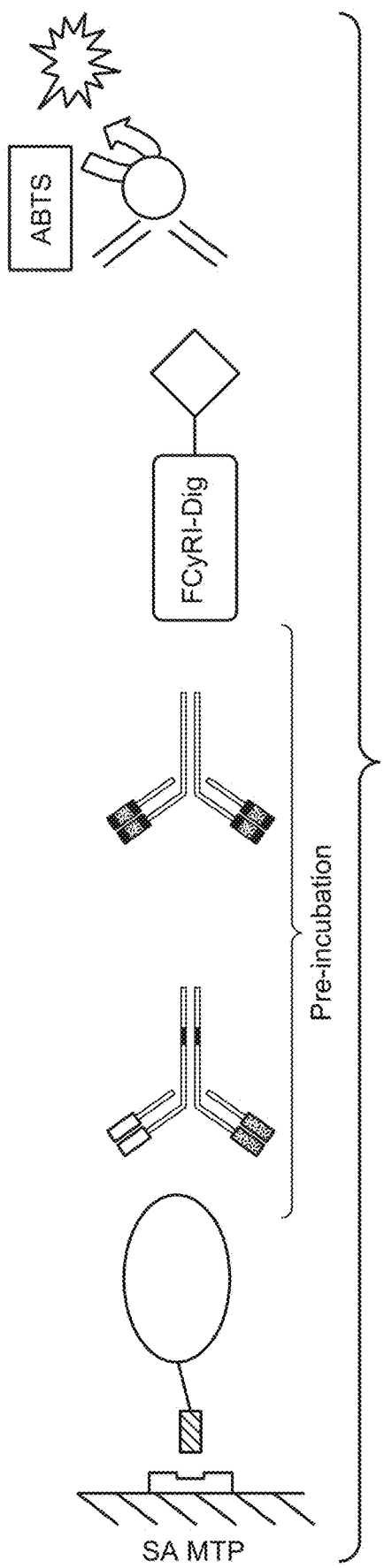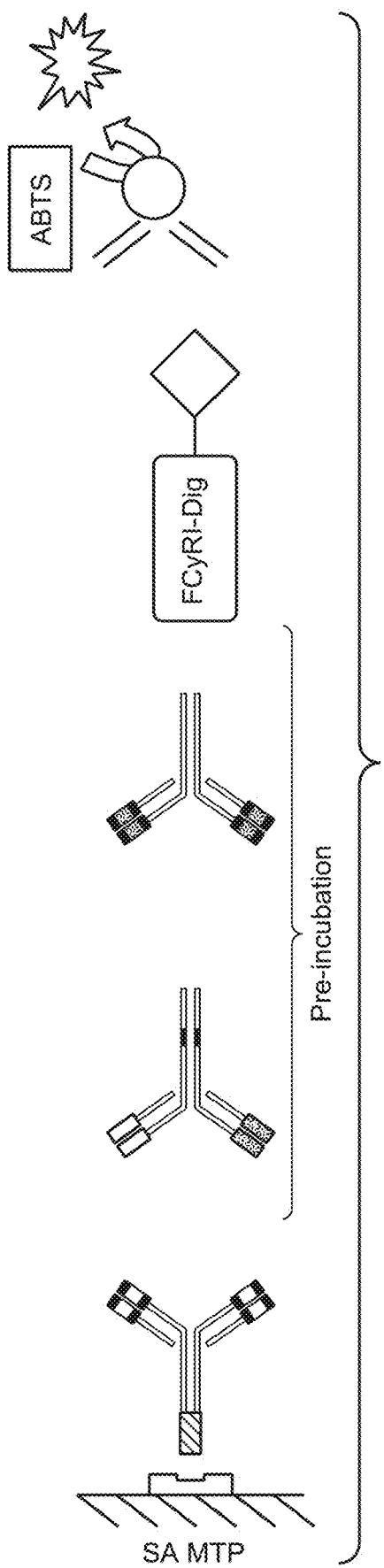

SEQUENCE LISTING

<160> NUMBER OF SEQ ID NOS: 5

<210> SEQ ID NO 1
<211> LENGTH: 359
<212> TYPE: PRT
<213> ORGANISM: Homo sapiens

<400> SEQUENCE: 1

```
Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
                20                  25                  30

Leu Pro Gly Ser Ser Ser Thr Gln Trp Phe Leu Asn Gly Thr Ala Thr
            35                  40                  45

Gln Thr Ser Thr Pro Ser Tyr Arg Ile Thr Ser Ala Ser Val Asn Asp
        50                  55                  60

Ser Gly Glu Tyr Arg Cys Gln Arg Gly Leu Ser Gly Arg Ser Asp Pro
65                  70                  75                  80

Ile Gln Leu Glu Ile His Arg Gly Trp Leu Leu Leu Gln Val Ser Ser
                85                  90                  95

Arg Val Phe Thr Glu Gly Glu Pro Leu Ala Leu Arg Cys His Ala Trp
                100                 105                 110

Lys Asp Lys Leu Val Tyr Asn Val Leu Tyr Tyr Arg Asn Gly Lys Ala
            115                 120                 125

Phe Lys Phe Phe His Trp Asn Ser Asn Leu Thr Ile Leu Lys Thr Asn
        130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
            180                 185                 190

Val Thr Leu Ser Cys Glu Thr Lys Leu Leu Leu Gln Arg Pro Gly Leu
        195                 200                 205
```

Gln Leu Tyr Phe Ser Phe Tyr Met Gly Ser Lys Thr Leu Arg Gly Arg
    210                 215                 220

Asn Thr Ser Ser Glu Tyr Gln Ile Leu Thr Ala Arg Arg Glu Asp Ser
225                 230                 235                 240

Gly Leu Tyr Trp Cys Glu Ala Ala Thr Glu Asp Gly Asn Val Leu Lys
                245                 250                 255

Arg Ser Pro Glu Leu Glu Leu Gln Val Leu Gly Leu Gln Leu Pro Thr
            260                 265                 270

Pro Val Trp Phe His Val Leu Phe Tyr Leu Ala Val Gly Ile Met Phe
        275                 280                 285

Leu Val Asn Thr Val Leu Trp Val Thr Ile Arg Lys Glu Leu Lys Arg
    290                 295                 300

Lys Lys Lys Trp Asp Leu Glu Ile Ser Leu Asp Ser Gly His Glu Lys
305                 310                 315                 320

Lys Val Ile Ser Ser Leu Gln Glu Asp Arg His Leu Glu Glu Glu Leu
                325                 330                 335

Lys Cys Gln Glu Gln Lys Glu Glu Gln Leu Gln Glu Gly Val His Arg
            340                 345                 350

Lys Glu Pro Gln Gly Ala Thr
        355

<210> SEQ ID NO 2
<211> LENGTH: 262
<212> TYPE: PRT
<213> ORGANISM: Homo sapiens

<400> SEQUENCE: 2

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
                20                  25                  30

Leu Pro Gly Ser Ser Ser Thr Gln Trp Phe Leu Asn Gly Thr Ala Thr
            35                  40                  45

Gln Thr Ser Thr Pro Ser Tyr Arg Ile Thr Ser Ala Ser Val Asn Asp
        50                  55                  60

Ser Gly Glu Tyr Arg Cys Gln Arg Gly Leu Ser Gly Arg Ser Asp Pro
65                  70                  75                  80

Ile Gln Leu Glu Ile His Arg Gly Trp Leu Leu Leu Gln Val Ser Ser
                85                  90                  95

Arg Val Phe Thr Glu Gly Glu Pro Leu Ala Leu Arg Cys His Ala Trp
            100                 105                 110

Lys Asp Lys Leu Val Tyr Asn Val Leu Tyr Tyr Arg Asn Gly Lys Ala
        115                 120                 125

Phe Lys Phe Phe His Trp Asn Ser Asn Leu Thr Ile Leu Lys Thr Asn
    130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
            180                 185                 190

Val Thr Leu Ser Cys Glu Thr Lys Leu Leu Leu Gln Arg Pro Gly Leu
        195                 200                 205

Gln Leu Tyr Phe Ser Phe Tyr Met Gly Ser Lys Thr Leu Arg Gly Arg

```
                210                 215                 220
Asn Thr Ser Ser Glu Tyr Gln Ile Leu Thr Ala Arg Arg Glu Asp Ser
225                 230                 235                 240

Gly Leu Tyr Trp Cys Glu Ala Ala Thr Glu Asp Gly Asn Val Leu Lys
            245                 250                 255

Arg Ser Pro Glu Leu Glu
            260

<210> SEQ ID NO 3
<211> LENGTH: 277
<212> TYPE: PRT
<213> ORGANISM: Homo sapiens

<400> SEQUENCE: 3

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
            20                  25                  30

Leu Pro Gly Ser Ser Ser Thr Gln Trp Phe Leu Asn Gly Thr Ala Thr
        35                  40                  45

Gln Thr Ser Thr Pro Ser Tyr Arg Ile Thr Ser Ala Ser Val Asn Asp
50                  55                  60

Ser Gly Glu Tyr Arg Cys Gln Arg Gly Leu Ser Gly Arg Ser Asp Pro
65                  70                  75                  80

Ile Gln Leu Glu Ile His Arg Gly Trp Leu Leu Leu Gln Val Ser Ser
                85                  90                  95

Arg Val Phe Thr Glu Gly Glu Pro Leu Ala Leu Arg Cys His Ala Trp
            100                 105                 110

Lys Asp Lys Leu Val Tyr Asn Val Leu Tyr Tyr Arg Asn Gly Lys Ala
        115                 120                 125

Phe Lys Phe Phe His Trp Asn Ser Asn Leu Thr Ile Leu Lys Thr Asn
130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
            180                 185                 190

Val Thr Leu Ser Cys Glu Thr Lys Leu Leu Leu Gln Arg Pro Gly Leu
        195                 200                 205

Gln Leu Tyr Phe Ser Phe Tyr Met Gly Ser Lys Thr Leu Arg Gly Arg
210                 215                 220

Asn Thr Ser Ser Glu Tyr Gln Ile Leu Thr Ala Arg Arg Glu Asp Ser
225                 230                 235                 240

Gly Leu Tyr Trp Cys Glu Ala Ala Thr Glu Asp Gly Asn Val Leu Lys
                245                 250                 255

Arg Ser Pro Glu Leu Glu Leu Gln Val Leu Gly Leu Gln Leu Pro Thr
            260                 265                 270

Pro Val Trp Phe His
        275

<210> SEQ ID NO 4
<211> LENGTH: 169
<212> TYPE: PRT
<213> ORGANISM: Homo sapiens
```

```
<400> SEQUENCE: 4

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
                20                  25                  30

Leu Pro Gly Ser Ser Thr Gln Trp Phe Leu Asn Gly Thr Ala Thr
            35                  40                  45

Gln Thr Ser Thr Pro Ser Tyr Arg Ile Thr Ser Ala Ser Val Asn Asp
        50                  55                  60

Ser Gly Glu Tyr Arg Cys Gln Arg Gly Leu Ser Gly Arg Ser Asp Pro
65                  70                  75                  80

Ile Gln Leu Glu Ile His Arg Gly Trp Leu Leu Leu Gln Val Ser Ser
                85                  90                  95

Arg Val Phe Thr Glu Gly Glu Pro Leu Ala Leu Arg Cys His Ala Trp
                100                 105                 110

Lys Asp Lys Leu Val Tyr Asn Val Leu Tyr Tyr Arg Asn Gly Lys Ala
            115                 120                 125

Phe Lys Phe His Trp Asn Ser Asn Leu Thr Ile Leu Lys Thr Asn
    130                 135                 140

Ile Ser His Asn Gly Thr Tyr His Cys Ser Gly Met Gly Lys His Arg
145                 150                 155                 160

Tyr Thr Ser Ala Gly Ile Ser Val Thr
                165

<210> SEQ ID NO 5
<211> LENGTH: 86
<212> TYPE: PRT
<213> ORGANISM: Homo sapiens

<400> SEQUENCE: 5

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
                20                  25                  30

Leu Pro Gly Ser Ser Thr Gln Trp Phe Leu Asn Gly Thr Ala Thr
            35                  40                  45

Gln Thr Ser Thr Pro Ser Tyr Arg Ile Thr Ser Ala Ser Val Asn Asp
        50                  55                  60

Ser Gly Glu Tyr Arg Cys Gln Arg Gly Leu Ser Gly Arg Ser Asp Pro
65                  70                  75                  80

Ile Gln Leu Glu Ile His
                85
```

METHOD FOR THE DETERMINATION OF ANTI-DRUG ANTIBODIES AGAINST AN EFFECTOR FUNCTION SUPPRESSED HUMAN OR HUMANIZED DRUG ANTIBODY

CROSS-REFERENCE TO RELATED APPLICATIONS

This application is a continuation of International Patent Application No. PCT/EP2015/074495, having an international filing date of Oct. 22, 2015, the entire contents of which are incorporated herein by reference, and which claims benefit under 35 U.S.C. § 119 to European Patent Application No. 14191806.0, filed on Nov. 5, 2014.

SEQUENCE LISTING

The instant application contains a Sequence Listing which has been submitted electronically in ASCII format and is hereby incorporated by reference in its entirety. Said ASCII copy, created on May 4, 2017, is named P32402-US_SequenceListing.txt and is 10,549 bytes in size.

BACKGROUND OF THE INVENTION

The current invention is directed to a method for the detection/determination of anti-drug antibodies in sample comprising mammalian serum using human Fcgamma receptor I or an Fc-region binding fragment thereof as specific detection reagent.

Standard solid-phase immunoassays with antibodies involve the formation of a complex between an antibody adsorbed/immobilized on a solid phase (capture antibody), the antigen, and an antibody to another epitope of the antigen conjugated with an enzyme or detectable label (tracer antibody). In the assay, a sandwich is formed: solid phase/capture antibody/antigen/tracer antibody. In the reaction catalyzed by the sandwich among other things the activity of the antibody-conjugated enzyme is proportional to the antigen concentration in the incubation medium. Anti-idiotypic antibody assays are mentioned, for example, in U.S. Pat. No. 5,219,730; WO 87/002778; EP 0 139 389; and EP 0 170 302. Wadhwa, M., et al. (J. Immunol. Methods 278 (2003) 1-17) report strategies for the detection, measurement and characterization of unwanted antibodies induced by therapeutic biologicals. A method for producing anti idiotypic antibodies is reported in EP 1 917 854.

Chen, Y.-P., et al. (Clin. Vac. Immunol. 14 (2007) 720-725) report the rapid detection of hepatitis B virus surface antigen by an agglutination assay mediated by a bispecific diabody against both human erythrocytes and hepatitis B virus surface antigen. Porter, R., et al report an electro-active system of immuno-assay (EASI assay) utilizing self-assembled monolayer modified electrodes (Biosensors Bioelec. 16 (2001) 9-12). The development of an enzyme immunoassay for the measurement of human tumor necrosis factor-alpha (hTNF-alpha) using bispecific antibodies to hTNF-alpha and horseradish peroxidase is reported by Berkova, N., et al. (Biotechnol. Appl. Biochem. 23 (1996) 163-171). In EP 0 962 771 a detection apparatus and method for the same is reported. Reinhartz, H. W., et al. (Analyst 121 (1996) 767-771) report bispecific multivalent antibody studied by real-time interaction analysis for the development of an antigen-inhibition enzyme-linked immunosorbent assay. The chemical generation of bispecific antibodies is reported by Doppalapudi, V. R., et al. (Proc. Natl. Acad. Sci. USA 107 (2010) 22611-22616).

In EP 2492689 A1 the detection of antibodies using an improved immune complex (IC) ELISA is reported. Methods for detecting antibodies are reported in WO 2011/135024. In WO 2009/077127 a distinguishing assay is reported. A method for detecting anti-drug antibodies is reported in EP 2351792. In WO 2012/130831 antibody Fc-variants are reported.

SUMMARY OF THE INVENTION

Herein is reported an immunoassay as well as a method and a use based on the specific binding of human Fcgamma receptor I to the Fc-region of an anti-drug antibody against an effector function suppressed human or humanized drug antibody for the determination of the presence as well as the amount of the anti-drug antibody.

It has been found that it is advantageous for the detection and quantification of anti-drug antibodies against an effector function suppressed human or humanized drug antibody to use the human Fcgamma receptor I or an Fc-region binding fragment thereof as one compound in an immunoassay. By using the human Fcgamma receptor I an improved immunoassay e.g. compared to a conventional bridging immunoassay, can be provided. The improvement being amongst other things an improved sensitivity and/or robustness.

The aspects as reported herein are especially useful if the drug antibody is an effector function suppressed human or humanized drug antibody, i.e. if the drug antibody's Fc-region (Fc-region polypeptides) contain mutations that reduce or even eliminate the drug antibody's binding to the human Fcgamma receptor III.

The human Fcgamma receptor I can be used as capture compound (when it is immobilized to a solid surface) or a tracer compound (when it is conjugated to a detectable label).

One aspect as reported herein is an anti-drug antibody immunoassay for the determination of the presence of an anti-drug antibody against an effector function suppressed human or humanized drug antibody in a sample comprising the following steps in the following order:
  incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and
  determining the complex formed in the previous step by the detectable label.

One aspect as reported herein is an anti-drug antibody immunoassay for the determination of the presence of an anti-drug antibody against an effector function suppressed human or humanized drug antibody in a sample comprising the following steps in the following order:
  incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, isolating the complex formed between the anti-drug antibody against the effector function suppressed human or humanized drug antibody and the human Fcgamma receptor I or the Fc-region binding fragment thereof, and determining the complex by the detectable label.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:

a) incubating a solid phase on which the effector function suppressed human or humanized drug antibody has been immobilized with a sample comprising mammalian blood serum (so that a solid-phase-bound drug antibody-anti-drug antibody complex is formed), b) incubating the solid phase (to which the drug antibody-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and c) determining the formation of a solid-phase-bound complex in step b) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:

a) incubating a solid phase on which the FAB of an effector function suppressed human or humanized drug antibody has been immobilized with a sample comprising mammalian blood serum (so that a solid-phase-bound FAB-anti-drug antibody complex is formed), b) incubating the solid phase (to which the FAB-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and c) determining the formation of a solid-phase bound complex in step b) by determining the presence of the detectable label and thereby determining the presence of an anti-drug antibody against an effector function suppressed human.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:

a) adding (excess) drug antibody to the sample (to transfer (any) anti-drug antibody present in the sample in a drug-antibody-anti-drug antibody complex), wherein the sample comprises mammalian blood serum, b) incubating a solid phase on which the antigen to which the EFS-DA specifically binds has been immobilized with the sample obtained in step a) (so that a solid-phase-bound antigen-drug antibody-anti-drug antibody complex is formed), c) incubating the solid phase (to which the antigen-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and d) determining the formation of a solid-phase-bound complex in step c) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:

a) adding (excess) drug antibody to the sample (to transfer (any) anti-drug antibody present in the sample in a drug-antibody-anti-drug antibody complex), wherein the sample comprises mammalian blood serum, b) incubating a solid phase on which full length human Fcgamma receptor I or an Fc-region binding fragment thereof has been immobilized with the sample obtained in step a) (so that a solid-phase-bound receptor-drug antibody-anti-drug antibody complex is formed), c) incubating the solid phase (to which the receptor-drug antibody-anti-drug antibody complex formed in step b) is bound) with the antigen of the drug antibody, whereby the antigen is conjugated to a detectable label, and d) determining the formation of a solid-phase-bound complex in step c) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:

a) adding (excess) drug antibody to the sample (to transfer (any) anti-drug antibody present in the sample in a drug-antibody-anti-drug antibody complex), wherein the sample comprises mammalian blood serum, b) incubating a solid phase on which an anti-drug antibody against the drug antibody has been immobilized with the sample obtained in step a) (so that a solid-phase-bound anti-drug antibody-drug antibody-anti-drug antibody complex is formed), c) incubating the solid phase (to which the anti-drug antibody-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and d) determining the formation of a solid-phase-bound complex in step c) by determining the presence of the detectable label and thereby determining the presence of an anti-drug antibody against an effector function suppressed human or humanized drug antibody in the sample.

One aspect as reported herein is a method for the determination of the presence of an anti-drug antibody against an effector function suppressed human or humanized drug antibody in a sample comprising the following steps in the following order:
- incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and
- determining the complex formed in the previous step by the detectable label.

In one embodiment of all aspects as reported herein the complex between the anti-drug antibody against the effector function suppressed human or humanized drug antibody present in the sample and the human Fcgamma receptor I or the Fc-region binding fragment thereof is a 1:1 complex. This means that exactly one anti-drug antibody against the effector function suppressed human or humanized drug antibody present in the sample and exactly one human Fcgamma receptor I or Fc-region binding fragment is present in the formed complex.

In one embodiment of all aspects as reported herein the complex between the anti-drug antibody against the effector function suppressed human or humanized drug antibody present in the sample and the human Fcgamma receptor I or the Fc-region binding fragment thereof is a monomeric complex. This means that none of the compounds in the complex is a multimer. This means further that no avidity effects are used in the aspects as reported herein.

In one embodiment of all aspects as reported herein all complexes formed are monomeric complexes.

In one embodiment of all aspects as reported herein all complexes formed is a 1:1 or 1:1:1 complex. This means that only a single molecule of each compound of which the complex is formed is present in the complex depending on the used complex format. In one embodiment, the complex comprises 1) exactly one molecule of the effector function suppressed human or humanized drug antibody, 2) exactly one molecule of the anti-drug antibody against the effector function suppressed human or humanized drug antibody, and 3) exactly one molecule of the human Fcgamma receptor I or the Fc-region binding fragment thereof. In one embodiment, the complex comprises 1) exactly one molecule of the effector function suppressed human or humanized drug antibody, 2) exactly one molecule of the antigen of the effector function suppressed human or humanized drug antibody, and 3) exactly one molecule of the human Fcgamma receptor I or the Fc-region binding fragment thereof. In one embodiment, the complex comprises 1) exactly one molecule of the effector function suppressed human or humanized drug antibody FAB, 2) exactly one molecule of the anti-drug antibody against the effector function suppressed human or humanized drug antibody, and 3) exactly one molecule of the human Fcgamma receptor I or the Fc-region binding fragment thereof.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
a) incubating a solid phase on which the effector function suppressed human or humanized drug antibody has been immobilized with a sample comprising mammalian blood serum (so that a monomeric 1:1 solid-phase-bound drug antibody-anti-drug antibody complex is formed),
b) incubating the solid phase (to which the drug antibody-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
c) determining the formation of a monomeric 1:1 solid-phase-bound complex in step b) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
a) incubating a solid phase on which the FAB of an effector function suppressed human or humanized drug antibody has been immobilized with a sample comprising mammalian blood serum (so that a monomeric 1:1 solid-phase-bound FAB-anti-drug antibody complex is formed),
b) incubating the solid phase (to which the FAB-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
c) determining the formation of a monomeric 1:1 solid-phase bound complex in step b) by determining the presence of the detectable label and thereby determining the presence of an anti-drug antibody against an effector function suppressed human.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
a) adding (excess) drug antibody to the sample (to transfer (any) anti-drug antibody present in the sample in a drug-antibody-anti-drug antibody complex), wherein the sample comprises mammalian blood serum,
b) incubating a solid phase on which the antigen to which the EFS-DA specifically binds has been immobilized with the sample obtained in step a) (so that a monomeric 1:1 solid-phase-bound antigen-drug antibody-anti-drug antibody complex is formed),
c) incubating the solid phase (to which the antigen-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
d) determining the formation of a monomeric 1:1 solid-phase-bound complex in step c) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) adding (excess) drug antibody to the sample (to transfer (any) anti-drug antibody present in the sample in a drug-antibody-anti-drug antibody complex), wherein the sample comprises mammalian blood serum,
- b) incubating a solid phase on which full length human Fcgamma receptor I or an Fc-region binding fragment thereof has been immobilized with the sample obtained in step a) (so that a monomeric 1:1 solid-phase-bound receptor-drug antibody-anti-drug antibody complex is formed),
- c) incubating the solid phase (to which the receptor-drug antibody-anti-drug antibody complex formed in step b) is bound) with the antigen of the drug antibody, whereby the antigen is conjugated to a detectable label, and
- d) determining the formation of a monomeric 1:1 solid-phase-bound complex in step c) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) adding (excess) drug antibody to the sample (to transfer (any) anti-drug antibody present in the sample in a drug-antibody-anti-drug antibody complex), wherein the sample comprises mammalian blood serum,
- b) incubating a solid phase on which an anti-drug antibody against the drug antibody has been immobilized with the sample obtained in step a) (so that a monomeric 1:1 solid-phase-bound anti-drug antibody-drug antibody-anti-drug antibody complex is formed),
- c) incubating the solid phase (to which the anti-drug antibody-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
- d) determining the formation of a monomeric 1:1 solid-phase-bound complex in step c) by determining the presence of the detectable label and thereby determining the presence of an anti-drug antibody against an effector function suppressed human or humanized drug antibody in the sample.

One aspect as reported herein is a method for the determination of the presence of an anti-drug antibody against an effector function suppressed human or humanized drug antibody in a sample comprising the following steps in the following order:
incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and
determining the complex formed in the previous step by the detectable label.

One aspect as reported herein is the use of human Fcgamma receptor I or an Fc-region binding fragment thereof for the determination of the presence or amount of an anti-drug antibody against an effector function suppressed human or humanized drug antibody in a sample comprising mammalian blood serum.

In one embodiment of all aspects as reported herein each incubating step is followed by the following step:
washing the solid phase to remove unbound compounds.

In one embodiment of all aspects as reported herein the assay is for the determination of the presence and the amount of an anti-drug antibody (ADA) against an effector function suppressed human or humanized drug antibody (EFS-DA) in a sample and comprises as final steps:
determining the formation of a solid-phase-bound complex in the previous step by determining the presence of the detectable label and determining the amount of an anti-drug antibody against an effector function suppressed human or humanized drug antibody in the sample by correlating the amount of the determined label with the amount of the anti-drug antibody using a standard curve.

In one embodiment of all aspects as reported herein the effector function suppressed human or humanized drug antibody is of the human IgG1 or IgG4 subclass.

In one embodiment of all aspects as reported herein the effector function suppressed human or humanized drug antibody is of the human IgG1 subclass and has the mutations L234A, L235A and P329G in both Fc-region polypeptides or the effector function suppressed human or humanized drug antibody is of the human IgG4 subclass and has the mutations S228P, L235E and P329G in both Fc-region polypeptides (numbering according to the EU numbering system according to Kabat).

In one embodiment of all aspects the effector function suppressed human or humanized drug antibody is a bispecific antibody, or a trispecific antibody, or a tetraspecific antibody, or a pentaspecific antibody, or a hexaspecific antibody. In one embodiment the effector function suppressed human or humanized drug antibody is a bispecific antibody.

In one embodiment of all aspects as reported herein the effector function suppressed human or humanized drug antibody does not induce ADCC.

In one embodiment of all aspects as reported herein the mammalian blood serum is human blood serum or cynomolgus blood serum or mouse blood serum.

In one embodiment of all aspects as reported herein the mammalian blood serum has been obtained from a mammal to which the effector function suppressed human or humanized drug antibody had been administered. In one embodiment the sample is obtained at least 2 days after the first administration of the antibody to the mammal.

In one embodiment of all aspects as reported herein the sample comprises of from 0.5% (v/v) to 8% (v/v) mammalian serum, preferably about 2% (v/v) mammalian serum.

In one embodiment of all aspects as reported herein the anti-drug antibody against an effector function suppressed human or humanized drug antibody is of the IgG class.

In one embodiment of all aspects as reported herein the presence and/or amount of the label is determined using an enzyme linked color reaction, surface plasmon resonance, electrochemiluminescence, or radioimmunoassay.

In one embodiment of all aspects as reported herein the immunoassay and/or the method and/or the use is an in vitro immunoassay and/or an in vitro method and/or an in vitro use.

In one embodiment of all aspects as reported herein the solid phase is conjugated to a first member of a binding pair and the compound to be immobilized on the solid phase is conjugated to the second member of a binding pair.

Such a binding pair (first member/second member) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc.

In one embodiment the second binding partner is bound (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc. In one embodiment the second binding partner is conjugated to biotin and immobilization is performed via immobilized avidin or streptavidin.

In one preferred embodiment the first member of a binding pair is streptavidin and the second member of a binding pair is biotin.

In one embodiment the solid phase is conjugated to streptavidin and the compound to be immobilized on the solid phase is biotinylated.

In one embodiment the solid phase is a streptavidin coated paramagnetic bead or a streptavidin coated sepharose bead or a streptavidin coated well of a multi-well-plate.

In one embodiment the compound to be conjugated to the solid phase is a mixture comprising at least two compounds that differ in the site at which they are conjugated to biotin and thereby thereafter immobilized on the solid phase.

In one embodiment the compound to be immobilized on the solid phase is conjugated to the second member of the binding pair by chemically binding via N-terminal and/or ε-amino groups (lysine), ε-amino groups of different lysins, carboxy-, sulfhydryl-, hydroxyl- and/or phenolic functional groups of the amino acid backbone of the polypeptide and/or sugar alcohol groups of the carbohydrate structure of the polypeptide.

Such conjugation via different amino groups can be performed by acylation of a part of the ε-amino groups with chemical protecting agents, e.g. by citraconylation, in a first step. In a second step conjugation is performed via the remaining amino groups. Subsequently citraconylation is removed and the binding partner is immobilized on the solid phase via remaining free amino groups, i.e. the binding partner obtained is immobilized on the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

DETAILED DESCRIPTION OF THE INVENTION

It has been found that it is advantageous for the detection and quantification of anti-drug antibodies against an effector function suppressed human or humanized drug antibody to use the human Fcgamma receptor I or an Fc-region binding fragment thereof as one compound in an immunoassay.

By using the human Fcgamma receptor I an improved immunoassay e.g. compared to a conventional bridging immunoassay, can be provided.

The improvement being without limitation in sensitivity and/or robustness.

In the assay as reported herein target interference is reduced and thereby the number of false positive results is reduced. Interference from IgM (e.g. originating from an early and/or non-specific immune response) is reduced.

With the assay as reported herein low affinity anti-drug antibodies can be detected.

The generally used bridging assay format for the determination of anti-drug antibodies requires that the anti-drug antibody can bind to two molecules of the drug antibody simultaneously.

In the immunoassay and method as reported herein the anti-drug antibody is not required to bridge two copies of the drug antibody. In fact the immunoassay and method as reported herein uses different binding sites in a sequential manner.

In more detail, the immunoassay as reported herein is improved among other things regarding sensitivity, required sample volume, binding mode of the compounds. Therewith the number of anti-drug antibodies recognized in the anti-drug antibody immunoassay is bigger than e.g. with a conventional bridging immunoassay as also non-bridging anti-drug antibodies are detected.

Further the immunoassay as reported herein has improved properties regarding the detection of anti-drug antibodies of the IgG class (secondary immune response) over anti-drug antibodies of the IgM class (primary immune response).

Herein is reported an anti-drug antibody immunoassay for the determination of the presence of an anti-drug antibody against an effector function suppressed human or humanized drug antibody in a sample comprising the following steps in the following order:

incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and determining the complex formed in the previous step by the detectable label.

The assay as reported herein provides for an improved method for the detection of effector function suppressed therapeutic drug antibodies. These effector function suppressed human or humanized drug antibodies (these are the only antibodies useful for therapy of a human patient) do not bind to human Fcgamma receptors or vice versa human Fcgamma receptors do not bind to the Fc-region of the effector function suppressed human or humanized drug antibodies as the binding site has been modified to suppress effector function which is mediated by human Fcgamma receptors.

Human Fcgamma receptor I (CD64) is a high affine (with respect to human Fc-region) receptor whereas human Fcgamma receptors II and III (CD32 and CD16, respectively) are low affinity receptors.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

In certain embodiments, the antibody is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies can be prepared as full length antibodies or antibody fragments. In one embodiment the antibody is a bispecific antibody which specifically binds to a first and a second antigen. In one embodiment the bispecific antibody has i) a first binding specificity that specifically binds to a first antigen or a first epitope on an antigen, and ii) a second binding specificity that specifically binds to a second antigen or a second epitope on the same antigen. In one embodiment the second epitope on the same antigen is a non-overlapping epitope.

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

An "antibody fragment" refers to any molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG1, IgG2, IgG3, IgG4, IgA1, and IgA2. The heavy chain constant domains that correspond to the different classes of immunoglobulins are called α, δ, ε, γ, and μ, respectively.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

The term "effector function suppressed human or humanized drug antibody" denotes an antibody that does not elicit ADCC.

In one embodiment an effector function suppressed antibody does not bind to human Fcgamma receptor III.

In one embodiment the effector function suppressed human or humanized drug antibody is of the subclass IgG1 or the subclass IgG4. In one embodiment the effector function suppressed human or humanized antibody of the subclass IgG1 comprises in the heavy chain constant region at position 234 and position 235 the amino acid residue alanine (numbering according to the Kabat EU index). In one embodiment the effector function suppressed human or humanized antibody comprises in the heavy chain constant region at position 234 and position 235 the amino acid residue alanine and at position 329 the amino acid residue glycine (numbering according to the Kabat EU index). In one embodiment the effector function suppressed human or humanized antibody of the subclass IgG4 comprises in the heavy chain constant region at position 235 the amino acid residue alanine and at position 228 the amino acid residue proline (numbering according to the Kabat EU index). In one embodiment the effector function suppressed human or humanized antibody comprises in the heavy chain constant region at position 235 the amino acid residue alanine, at position 228 the amino acid residue proline and at position 329 the amino acid residue glycine (numbering according to the Kabat EU index).

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g. CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, E. A. et al., Sequences of Proteins of Immunological Interest, 5th ed. Public Health Service, National Institutes of Health, Bethesda, Md. (1991), NIH Publication 91-3242). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro, J. C. and Fransson, J., Front. Biosci. 13 (2008) 1619-1633). Unless otherwise indicated, HVR residues and other residues in the variable domain (e.g. FR residues) are numbered herein according to Kabat et al., supra.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "anti-idiotypic antibody" denotes an antibody, which specifically binds to a binding specificity such as a binding site of a parent antibody, i.e. which is directed e.g. against an antigen binding site of a parent antibody. In one embodiment the anti-idiotypic antibody specifically binds to one or more of the CDRs of the parent antibody. In one embodiment the parent antibody is a therapeutic antibody. In one embodiment the parent antibody is a multispecific antibody. In one embodiment the parent antibody is a bispecific antibody.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Polypeptides and monoclonal antibodies and their constant domains contain a number of reactive amino acid side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of polypeptides and antibodies is the aliphatic ε-amine of the amino acid lysine. In general, nearly all polypeptides and antibodies contain abundant lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of amino acids to form amide linkages. The anhydride rings open to create multivalent, metal-chelating arms able to bind tightly to metals in a coordination complex.

Another common reactive group in polypeptides and antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio) propionamido] hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in polypeptides and antibodies are carboxylic acids. Polypeptides and antibodies contain carboxylic acid groups at the C-terminal position and within the side chains of aspartic acid and glutamic acid. The relatively low reactivity of carboxylic acids in water usually makes it difficult to use these groups to selectively modify polypeptides and antibodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiff's base intermediate is formed, which can be reduced to an alkyl amine through the reduction of the intermediate with sodium cyanoborohydride (mild and selective) or sodium borohydride (strong) water-soluble reducing agents.

The term "sample" includes, but is not limited to, any quantity of a substance from a living thing or formerly living thing. Such living things include, but are not limited to, humans, mice, monkeys, rats, rabbits, and other animals. In one embodiment the sample is obtained from a monkey, especially a cynomolgus monkey, or a rabbit, or a mouse, or rat, or a human. Such substances include, but are not limited to, in one embodiment whole blood or serum from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxygenin, the detectable label is selected in one embodiment. The detectable label can also be a photoactivatable crosslinking group, e.g. an azido or an azirine group. Metal chelates which can be detected by electrochemiluminescence are also in one embodiment signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

Herein is reported a method for the determination of the presence and amount of an anti-drug antibody against an effector function suppressed human or humanized drug antibody in a sample comprising mammalian serum using human Fcgamma receptor I.

The term "human Fcgamma receptor I" denotes a transmembrane domain protein of SEQ ID NO: 01 (see also UniProt entry P12341, FCGR1A). Human Fcgamma receptor I is also termed cluster of differentiation 64 (CD64). It binds to the Fc-region of immunoglobulins gamma with high affinity. Human Fcgamma receptor I, which mediates antibody dependent cellular cytotoxicity and immune complex clearance, plays an important role in immunity and in resistance to infections in both man and mouse. The human Fcgamma receptor I used in the immunoassay and method as reported herein can be an Fc-region binding fragment of the full length human Fcgamma receptor I, such as e.g. in one embodiment only the three extracellular domains. In one embodiment the human Fcgamma receptor I has the amino acid sequence of SEQ ID NO: 01. In one embodiment the human Fcgamma receptor I has the amino acid sequence of SEQ ID NO: 02. In one preferred embodiment the human Fcgamma receptor I has the amino acid sequence of SEQ ID NO: 03.

One aspect as reported herein is an anti-drug antibody immunoassay for the determination of the presence of an anti-drug antibody against an effector function suppressed human or humanized drug antibody in a sample comprising the following steps in the following order:
  incubating a sample comprising mammalian blood serum
    with full length human Fcgamma receptor I or an
    Fc-region binding fragment thereof so that a complex
    between the anti-drug antibody against the effector
    function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and determining the complex formed in the previous step by the detectable label.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) incubating a solid phase on which the effector function suppressed human or humanized drug antibody has been immobilized with a sample comprising mammalian blood serum (so that a solid-phase-bound drug antibody-anti-drug antibody complex is formed),
- b) incubating the solid phase (to which the drug antibody-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
- c) determining the formation of a solid-phase-bound complex in step b) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) incubating a solid phase on which the FAB of an effector function suppressed human or humanized drug antibody has been immobilized with a sample comprising mammalian blood serum (so that a solid-phase-bound FAB-anti-drug antibody complex is formed),
- b) incubating the solid phase (to which the FAB-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
- c) determining the formation of a solid-phase bound complex in step b) by determining the presence of the detectable label and thereby determining the presence of an anti-drug antibody against an effector function suppressed human.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) adding (excess) drug antibody to the sample (to transfer (any) anti-drug antibody present in the sample in a drug-antibody-anti-drug antibody complex), wherein the sample comprises mammalian blood serum,
- b) incubating a solid phase on which the antigen to which the EFS-DA specifically binds has been immobilized with the sample obtained in step a) (so that a solid-phase-bound antigen-drug antibody-anti-drug antibody complex is formed),
- c) incubating the solid phase (to which the antigen-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
- d) determining the formation of a solid-phase-bound complex in step c) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) adding (excess) drug antibody to the sample (to transfer (any) anti-drug antibody present in the sample in a drug-antibody-anti-drug antibody complex), wherein the sample comprises mammalian blood serum,
- b) incubating a solid phase on which full length human Fcgamma receptor I or an Fc-region binding fragment thereof has been immobilized with the sample obtained in step a) (so that a solid-phase-bound receptor-drug antibody-anti-drug antibody complex is formed),
- c) incubating the solid phase (to which the receptor-drug antibody-anti-drug antibody complex formed in step b) is bound) with the antigen of the drug antibody, whereby the antigen is conjugated to a detectable label, and
- d) determining the formation of a solid-phase-bound complex in step c) by determining the presence of the detectable label and thereby determining the presence of an anti-drug antibody against an effector function suppressed human or humanized drug antibody in the sample.

One aspect as reported herein is an anti-drug antibody immunoassay for the determination of the presence of an anti-drug antibody (ADA) against an effector function suppressed human or humanized drug antibody (EFS-DA) in a sample comprising the following steps in the following order:
- a) adding (excess) drug antibody to the sample (to transfer (any) anti-drug antibody present in the sample in a drug-antibody-anti-drug antibody complex), wherein the sample comprises mammalian blood serum,
- b) incubating a solid phase on which an anti-drug antibody against the drug antibody has been immobilized with the sample obtained in step a) (so that a solid-phase-bound anti-drug antibody-drug antibody-anti-drug antibody complex is formed),
- c) incubating the solid phase (to which the anti-drug antibody-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
- d) determining the formation of a solid-phase-bound complex in step c) by determining the presence of the detectable label and thereby determining the presence of an anti-drug antibody against an effector function suppressed human or humanized drug antibody in the sample.

One aspect as reported herein is a method for the determination of the presence of an anti-drug antibody against an effector function suppressed human or humanized drug antibody in a sample comprising the following steps in the following order:

incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and determining the complex formed in the previous step by the detectable label.

One aspect as reported herein is the use of human Fcgamma receptor I or an Fc-region binding fragment thereof for the determination of the presence or amount of an anti-drug antibody against an effector function suppressed human or humanized drug antibody in a sample comprising mammalian blood serum.

Some compounds as used in the immunoassay and method as reported herein are conjugated to a member of a binding pair. The conjugation is in one embodiment performed by chemical binding via N-terminal and/or ε-amino groups (lysine), ε-amino groups of different lysins, carboxy-, sulfhydryl-, hydroxyl- and/or phenolic functional groups of the amino acid backbone of the compound and/or sugar alcohol groups of the carbohydrate structure of the compound. The conjugated compound is in one embodiment a mixture of at least two compounds conjugated to a member of a binding pair, wherein the at least two compounds in the mixture differ in the site at which they are conjugated to the member of the binding pair. For example, the mixture may comprise a conjugation via an amino acid of the amino acid backbone and a conjugation via a sugar alcohol group of a carbohydrate. Also, for example, the mixture may comprise compounds conjugated to the member of a binding pair via different amino acid residues of the amino acid backbone. The expression "different amino acid residue" denotes either two different kinds of amino acids, such as e.g. lysine and aspartic acid, or tyrosine and glutamic acid, or two amino acid residues of the amino acid backbone differing in their position in the amino acid sequence of the compound. In the latter case the amino acid can be of the same kind or of different kind. The expression "differ in the site" denotes a difference either in the kind of site, e.g. amino acid or sugar alcohol group, or in the number of the amino acid of the amino acid backbone, e.g. at which the compound is conjugated to the member of the binding pair.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype and the Kabat EU index numbering system (see pages 661-723) is used for the constant heavy chain domains (CH1, Hinge, CH2 and CH3).

SPECIFIC EMBODIMENTS OF THE INVENTION

1. An anti-drug antibody immunoassay for the determination of the presence of an anti-drug antibody against an effector function suppressed human or humanized drug antibody in a sample comprising the following steps in the following order:

incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and determining the complex formed in the previous step by the detectable label.

2. An anti-drug antibody immunoassay for the determination of the presence of an anti-drug antibody (ADA) against an effector function suppressed human or humanized drug antibody (EFS-DA) in a sample comprising the following steps in the following order:

a) incubating a solid phase on which the effector function suppressed human or humanized drug antibody has been immobilized with a sample comprising mammalian blood serum (so that a solid-phase-bound drug antibody-anti-drug antibody complex is formed), b) incubating the solid phase (to which the drug antibody-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and c) determining the formation of a solid-phase-bound complex in step b) by determining the presence of the detectable label and thereby determining the presence of an anti-drug antibody against an effector function suppressed human or humanized drug antibody in the sample.

3. An anti-drug antibody immunoassay for the determination of the presence of an anti-drug antibody (ADA) against an effector function suppressed human or humanized drug antibody (EFS-DA) in a sample comprising the following steps in the following order:

a) incubating a solid phase on which the FAB of an effector function suppressed human or humanized drug antibody has been immobilized with a sample comprising mammalian blood serum (so that a solid-phase-bound FAB-anti-drug antibody complex is formed), b) incubating the solid phase (to which the FAB-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and c) determining the formation of a solid-phase bound complex in step b) by determining the presence of the detectable label and thereby determining the presence of an anti-drug antibody against an effector function suppressed human 4. An anti-drug antibody immunoassay for the determination of the presence of an anti-drug antibody (ADA) against an effector function suppressed human or humanized drug antibody (EFS-DA) in a sample comprising the following steps in the following order:
   a) adding (excess) drug antibody to the sample (to transfer (any) anti-drug antibody present in the sample in a drug-antibody-anti-drug antibody complex), wherein the sample comprises mammalian blood serum,
   b) incubating a solid phase on which the antigen to which the EFS-DA specifically binds has been immobilized with the sample obtained in step a) (so that a solid-phase-bound antigen-drug antibody-anti-drug antibody complex is formed),
   c) incubating the solid phase (to which the antigen-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
   d) determining the formation of a solid-phase-bound complex in step c) by determining the presence of the detectable label and thereby determining the presence of an anti-drug antibody against an effector function suppressed human or humanized drug antibody in the sample.

5. An anti-drug antibody immunoassay for the determination of the presence of an anti-drug antibody (ADA) against an effector function suppressed human or humanized drug antibody (EFS-DA) in a sample comprising the following steps in the following order:
   a) adding (excess) drug antibody to the sample (to transfer (any) anti-drug antibody present in the sample in a drug-antibody-anti-drug antibody complex), wherein the sample comprises mammalian blood serum,
   b) incubating a solid phase on which full length human Fcgamma receptor I or an Fc-region binding fragment thereof has been immobilized with the sample obtained in step a) (so that a solid-phase-bound receptor-drug antibody-anti-drug antibody complex is formed),
   c) incubating the solid phase (to which the receptor-drug antibody-anti-drug antibody complex formed in step b) is bound) with the antigen of the drug antibody, whereby the antigen is conjugated to a detectable label, and
   d) determining the formation of a solid-phase-bound complex in step c) by determining the presence of the detectable label and thereby determining the presence of an anti-drug antibody against an effector function suppressed human or humanized drug antibody in the sample.

6. An anti-drug antibody immunoassay for the determination of the presence of an anti-drug antibody (ADA) against an effector function suppressed human or humanized drug antibody (EFS-DA) in a sample comprising the following steps in the following order:
   a) adding (excess) drug antibody to the sample (to transfer (any) anti-drug antibody present in the sample in a drug-antibody-anti-drug antibody complex), wherein the sample comprises mammalian blood serum,
   b) incubating a solid phase on which an anti-drug antibody against the drug antibody has been immobilized with the sample obtained in step a) (so that a solid-phase-bound anti-drug antibody-drug antibody-anti-drug antibody complex is formed),
   c) incubating the solid phase (to which the anti-drug antibody-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
   d) determining the formation of a solid-phase-bound complex in step c) by determining the presence of the detectable label and thereby determining the presence of an anti-drug antibody against an effector function suppressed human or humanized drug antibody in the sample.

7. The immunoassay according to any one of the preceding items, wherein each incubating step is followed by the following step:
   washing the solid phase to remove unbound compounds.

8. The immunoassay according to any one of the preceding items, wherein the assay is for the determination of the presence and the amount of an anti-drug antibody (ADA) against an effector function suppressed human or humanized drug antibody (EFS-DA) in a sample and comprises as final steps:
   determining the formation of a solid-phase-bound complex in the previous step by determining the presence of the detectable label and determining the amount of an anti-drug antibody against an effector function suppressed human or humanized drug antibody in the sample by correlating the amount of the determined label with the amount of the anti-drug antibody using a standard curve.

9. The immunoassay according to any one of the preceding items, wherein the effector function suppressed human or humanized drug antibody is of the human subclass IgG1 or IgG4.

10. The immunoassay according to any one of the preceding items, wherein the effector function suppressed human or humanized drug antibody is of the human subclass IgG1 and has the mutations L234A, L235A and P329G in both Fc-region polypeptides or wherein the effector function suppressed human or humanized drug antibody is of the human subclass IgG4 and has the mutations S228P, L235E and P329G in both Fc-region polypeptides (numbering according to the Kabat EU index).

11. The immunoassay according to any one of the preceding items, wherein the effector function suppressed human or humanized drug antibody is a bispecific antibody.

12. The immunoassay according to any one of the preceding items, wherein the effector function suppressed human or humanized drug antibody does not induce ADCC.

13. The immunoassay according to any one of the preceding items, wherein the mammalian blood serum is human blood serum or cynomolgus blood serum.

14. The immunoassay according to any one of the preceding items, wherein the mammalian blood serum has been obtained from a mammal to which the effector function suppressed human or humanized drug antibody had been administered for the first time at least 2 days prior to obtaining the sample.

15. The immunoassay according to any one of the preceding items, wherein the sample comprises of from 0.5% (v/v) to 8% (v/v) mammalian serum, preferably about 2% (v/v) mammalian serum.

16. The immunoassay according to any one of the preceding items, wherein the anti-drug antibody against an effector function suppressed human or humanized drug antibody is of the IgG class.

17. The immunoassay according to any one of the preceding items, wherein the presence and/or amount of the label is determined using an enzyme linked color reaction, surface plasmon resonance, electrochemiluminescence, or radioimmunoassay.

18. A method for the determination of the presence of an anti-drug antibody against an effector function suppressed human or humanized drug antibody in a sample comprising the following steps in the following order:
   incubating a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and
   determining the complex formed in the previous step by the detectable label.

19. A method for the determination of the presence of an anti-drug antibody (ADA) against an effector function suppressed human or humanized drug antibody (EFS-DA) in a sample comprising the following steps in the following order:
   a) incubating a solid phase on which the effector function suppressed human or humanized drug antibody has been immobilized with a sample comprising mammalian blood serum (so that a solid-phase-bound drug antibody-anti-drug antibody complex is formed),
   b) incubating the solid phase (to which the drug antibody-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
   c) determining the formation of a solid-phase-bound complex in step b) by determining the presence of the detectable label and thereby determining the presence of an anti-drug antibody against an effector function suppressed human or humanized drug antibody in the sample.

20. A method for the determination of the presence of an anti-drug antibody (ADA) against an effector function suppressed human or humanized drug antibody (EFS-DA) in a sample comprising the following steps in the following order:
   a) incubating a solid phase on which the FAB of an effector function suppressed human or humanized drug antibody has been immobilized with a sample comprising mammalian blood serum (so that a solid-phase-bound FAB-anti-drug antibody complex is formed),
   b) incubating the solid phase (to which the FAB-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
   c) determining the formation of a solid-phase bound complex in step b) by determining the presence of the detectable label and thereby determining the presence of an anti-drug antibody against an effector function suppressed human 21. A method for the determination of the presence of an anti-drug antibody (ADA) against an effector function suppressed human or humanized drug antibody (EFS-DA) in a sample comprising the following steps in the following order:
   a) adding (excess) drug antibody to the sample (to transfer (any) anti-drug antibody present in the sample in a drug-antibody-anti-drug antibody complex), wherein the sample comprises mammalian blood serum,
   b) incubating a solid phase on which the antigen to which the EFS-DA specifically binds has been immobilized with the sample obtained in step a) (so that a solid-phase-bound antigen-drug antibody-anti-drug antibody complex is formed),
   c) incubating the solid phase (to which the antigen-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
   d) determining the formation of a solid-phase-bound complex in step c) by determining the presence of the detectable label and thereby determining the presence of an anti-drug antibody against an effector function suppressed human or humanized drug antibody in the sample.

22. A method for the determination of the presence of an anti-drug antibody (ADA) against an effector function suppressed human or humanized drug antibody (EFS-DA) in a sample comprising the following steps in the following order:
   a) adding (excess) drug antibody to the sample (to transfer (any) anti-drug antibody present in the sample in a drug-antibody-anti-drug antibody complex), wherein the sample comprises mammalian blood serum,
   b) incubating a solid phase on which full length human Fcgamma receptor I or an Fc-region binding fragment thereof has been immobilized with the sample obtained in step a) (so that a solid-phase-bound receptor-drug antibody-anti-drug antibody complex is formed),
   c) incubating the solid phase (to which the receptor-drug antibody-anti-drug antibody complex formed in step b) is bound) with the antigen of the drug antibody, whereby the antigen is conjugated to a detectable label, and
   d) determining the formation of a solid-phase-bound complex in step c) by determining the presence of the detectable label and thereby determining the presence of an anti-drug antibody against an effector function suppressed human or humanized drug antibody in the sample.

23. A method for the determination of the presence of an anti-drug antibody (ADA) against an effector function suppressed human or humanized drug antibody (EFS-DA) in a sample comprising the following steps in the following order:
   a) adding (excess) drug antibody to the sample (to transfer (any) anti-drug antibody present in the sample in a drug-antibody-anti-drug antibody complex), wherein the sample comprises mammalian blood serum,
   b) incubating a solid phase on which an anti-drug antibody against the drug antibody has been immobilized with the sample obtained in step a) (so that a solid-phase-bound anti-drug antibody-drug antibody-anti-drug antibody complex is formed),
   c) incubating the solid phase (to which the anti-drug antibody-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and d) determining the formation of a solid-phase-bound complex in step c) by determining the presence of the detectable label and thereby determining the presence of an anti-drug antibody against an effector function suppressed human or humanized drug antibody in the sample.

24. The method according to any one of items 18 to 23, wherein each incubating step is followed by the following step:
washing the solid phase to remove unbound compounds.

25. The method according to any one of items 18 to 24, wherein the assay is for the determination of the presence and the amount of an anti-drug antibody (ADA) against an effector function suppressed human or humanized drug antibody (EFS-DA) in a sample and comprises as final steps:
determining the formation of a solid-phase-bound complex in the previous step by determining the presence of the detectable label and determining the amount of an anti-drug antibody against an effector function suppressed human or humanized drug antibody in the sample by correlating the amount of the determined label with the amount of the anti-drug antibody using a standard curve.

26. The method according to any one of items 18 to 25, wherein the effector function suppressed human or humanized drug antibody is of the human subclass IgG1 or IgG4.

27. The method according to any one of items 18 to 26, wherein the effector function suppressed human or humanized drug antibody is of the human subclass IgG1 and has the mutations L234A, L235A and P329G in both Fc-region polypeptides or wherein the effector function suppressed human or humanized drug antibody is of the human subclass IgG4 and has the mutations S228P, L235E and P329G in both Fc-region polypeptides (numbering according to the Kabat EU index).

28. The method according to any one of items 18 to 27, wherein the effector function suppressed human or humanized drug antibody is a bispecific antibody.

29. The method according to any one of items 18 to 28, wherein the effector function suppressed human or humanized drug antibody does not induce ADCC.

30. The method according to any one of items 18 to 29, wherein the mammalian blood serum is human blood serum or cynomolgus blood serum.

31. The method according to any one of items 18 to 30, wherein the mammalian blood serum has been obtained from a mammal to which the effector function suppressed human or humanized drug antibody had been administered at least 2 days prior to obtaining the sample.

32. The method according to any one of items 18 to 31, wherein the sample comprises of from 0.5% (v/v) to 8% (v/v) mammalian serum, preferably about 2% (v/v) mammalian serum.

33. The method according to any one of items 18 to 32, wherein the anti-drug antibody against an effector function suppressed human or humanized drug antibody is of the IgG class.

34. The method according to any one of items 18 to 33, wherein the presence and/or amount of the label is determined using an enzyme linked color reaction, surface plasmon resonance, electrochemiluminescence, or radioimmunoassay.

35. Use of human Fcgamma receptor I or an Fc-region binding fragment thereof for the determination of the presence or amount of an anti-drug antibody against an effector function suppressed human or humanized drug antibody in a sample comprising mammalian blood serum.

36. Use of human Fcgamma receptor I or an Fc-region binding fragment thereof for the determination of the presence of an anti-drug antibody against an effector function suppressed human or humanized drug antibody in a sample comprising the
incubation of a sample comprising mammalian blood serum with full length human Fcgamma receptor I or an Fc-region binding fragment thereof so that a complex between the anti-drug antibody against the effector function suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and
the determination of the complex formed in the previous step by the detectable label.

37. Use of human Fcgamma receptor I or an Fc-region binding fragment thereof for the determination of the presence of an anti-drug antibody (ADA) against an effector function suppressed human or humanized drug antibody (EFS-DA) in a sample comprising the:
a) incubation of a solid phase on which the effector function suppressed human or humanized drug antibody has been immobilized with a sample comprising mammalian blood serum (so that a solid-phase-bound drug antibody-anti-drug antibody complex is formed),
b) incubation of the solid phase (to which the drug antibody-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
c) the determination of the formation of a solid-phase-bound complex in step b) by determining the presence of the detectable label and thereby determining the presence of an anti-drug antibody against an effector function suppressed human or humanized drug antibody in the sample.

38. Use of human Fcgamma receptor I or an Fc-region binding fragment thereof for the determination of the presence of an anti-drug antibody (ADA) against an effector function suppressed human or humanized drug antibody (EFS-DA) in a sample comprising the:
a) incubation of a solid phase on which the FAB of an effector function suppressed human or humanized drug antibody has been immobilized with a sample comprising mammalian blood serum (so that a solid-phase-bound FAB-anti-drug antibody complex is formed),
b) incubation of the solid phase (to which the FAB-anti-drug antibody complex formed in step a) is bound) with full length human Fcgamma receptor I or an Fc-region binding fragment thereof, whereby the full length human Fcgamma receptor I or the Fc-region binding fragment thereof is conjugated to a detectable label, and
c) determination of the formation of a solid-phase bound complex in step b) by determining the presence of the detectable label and thereby determining the presence of an anti-drug antibody against an effector function suppressed human 39. Use of human Fcgamma receptor I or an Fc-region binding fragment thereof for the determination of the presence of an anti-drug antibody (ADA) against an effector function suppressed human or humanized drug antibody (EFS-DA) in a sample comprising the:
  a) addition of (excess) drug antibody to the sample (to transfer (any) anti-drug antibody present in the sample in a drug-antibody-anti-drug antibody complex), wherein the sample comprises mammalian blood serum,
  b) incubation of a solid phase on which the antigen to which the EFS-DA specifically binds has been immobilized with the sample obtained in step a) (so that a solid-phase-bound antigen-drug antibody-anti-drug antibody complex is formed),
  c) incubation of the solid phase (to which the antigen-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
  d) determination of the formation of a solid-phase-bound complex in step c) by determining the presence of the detectable label and thereby determining the presence of an anti-drug antibody against an effector function suppressed human or humanized drug antibody in the sample.

40. Use of human Fcgamma receptor I or an Fc-region binding fragment thereof for the determination of the presence of an anti-drug antibody (ADA) against an effector function suppressed human or humanized drug antibody (EFS-DA) in a sample comprising the:
  a) addition of (excess) drug antibody to the sample (to transfer (any) anti-drug antibody present in the sample in a drug-antibody-anti-drug antibody complex), wherein the sample comprises mammalian blood serum,
  b) incubation of a solid phase on which full length human Fcgamma receptor I or an Fc-region binding fragment thereof has been immobilized with the sample obtained in step a) (so that a solid-phase-bound receptor-drug antibody-anti-drug antibody complex is formed),
  c) incubation of the solid phase (to which the receptor-drug antibody-anti-drug antibody complex formed in step b) is bound) with the antigen of the drug antibody, whereby the antigen is conjugated to a detectable label, and
  d) determination of the formation of a solid-phase-bound complex in step c) by determining the presence of the detectable label and thereby determining the presence of an anti-drug antibody against an effector function suppressed human or humanized drug antibody in the sample.

41. Use of human Fcgamma receptor I or an Fc-region binding fragment thereof for the determination of the presence of an anti-drug antibody (ADA) against an effector function suppressed human or humanized drug antibody (EFS-DA) in a sample comprising the:
  a) addition of (excess) drug antibody to the sample (to transfer (any) anti-drug antibody present in the sample in a drug-antibody-anti-drug antibody complex), wherein the sample comprises mammalian blood serum,
  b) incubation of a solid phase on which an anti-drug antibody against the drug antibody has been immobilized with the sample obtained in step a) (so that a solid-phase-bound anti-drug antibody-drug antibody-anti-drug antibody complex is formed),
  c) incubation of the solid phase (to which the anti-drug antibody-drug antibody-anti-drug antibody complex formed in step b) is bound) with full length human Fcgamma receptor I or an Fc-region binding fragment thereof, whereby the full length human Fcgamma receptor I or the Fc-region binding fragment thereof is conjugated to a detectable label, and
  d) determination of the formation of a solid-phase-bound complex in step c) by determining the presence of the detectable label and thereby determining the presence of an anti-drug antibody against an effector function suppressed human or humanized drug antibody in the sample.

42. The use according to any one of items 35 to 41, wherein each incubation is followed by
  washing of the solid phase to remove unbound compounds.

43. The use according to any one of items 35 to 42, wherein the use is for the determination of the presence and the amount of an anti-drug antibody (ADA) against an effector function suppressed human or humanized drug antibody (EFS-DA) in a sample and comprises as final steps:
  the determination of the formation of a solid-phase-bound complex in the previous step by determining the presence of the detectable label and the determination of the amount of an anti-drug antibody against an effector function suppressed human or humanized drug antibody in the sample by correlating the amount of the determined label with the amount of the anti-drug antibody using a standard curve.

44. The use according to any one of items 35 to 43, wherein the effector function suppressed human or humanized drug antibody is of the human subclass IgG1 or IgG4.

45. The use according to any one of items 35 to 44, wherein the effector function suppressed human or humanized drug antibody is of the human subclass IgG1 and has the mutations L234A, L235A and P329G in both Fc-region polypeptides or wherein the effector function suppressed human or humanized drug antibody is of the human subclass IgG4 and has the mutations S228P, L235E and P329G in both Fc-region polypeptides (numbering according to the Kabat EU index).

46. The use according to any one of items 35 to 45, wherein the effector function suppressed human or humanized drug antibody is a bispecific antibody.

47. The use according to any one of items 35 to 46, wherein the effector function suppressed human or humanized drug antibody does not induce ADCC.

48. The use according to any one of items 35 to 47, wherein the mammalian blood serum is human blood serum or cynomolgus blood serum.

49. The use according to any one of items 35 to 48, wherein the mammalian blood serum has been obtained from a mammal to which the effector function suppressed human or humanized drug antibody had been administered for this first time at least 2 days prior to obtaining the sample.

50. The use according to any one of items 35 to 49, wherein the sample comprises of from 0.5% (v/v) to 8% (v/v) mammalian serum, preferably about 2% (v/v) mammalian serum.

51. The use according to any one of items 35 to 50, wherein the anti-drug antibody against an effector function suppressed human or humanized drug antibody is of the IgG class.

52. The use according to any one of items 35 to 51, wherein the presence and/or amount of the label is determined using an enzyme linked color reaction, surface plasmon resonance, electrochemiluminescence, or radioimmunoassay.
53. The method or the use according to any one of items 1 to 52, wherein the human Fcgamma receptor I has the amino acid sequence of SEQ ID NO: 01.
54. The method or the use according to any one of items 1 to 52, wherein the human Fcgamma receptor I has the amino acid sequence of SEQ ID NO: 02.

The following examples and figures are provided to aid the understanding of the present invention, the true scope of which is set forth in the appended claims. It is understood that modifications can be made in the procedures set forth without departing from the spirit of the invention.

BRIEF DESCRIPTION OF THE FIGURES

FIG. 1—Scheme of an anti-drug antibody assay using human FcγRI according to the invention.
FIG. 2—Scheme of anti-drug antibody assay using a conventional bridging assay format.
FIG. 8 A-C—Time course of the anti-drug antibody assay results determined with an assay according to the current invention (1) and with a conventional bridging assay (2);
FIG. 9—Scheme of an anti-drug antibody assay using human FcγRI according to the invention.
FIG. 10—Scheme of an anti-drug antibody assay using human FcγRI according to the invention.

EXAMPLE 1

Figure 3:
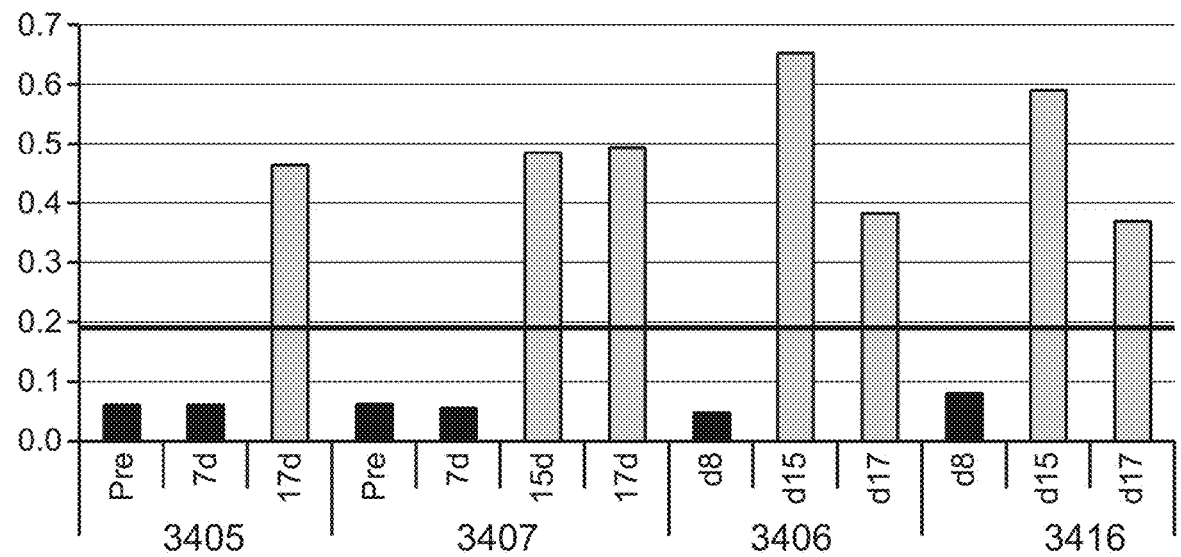
FIG. 3—Anti-drug antibody assay result of thirteen samples determined with the anti-drug antibody assay according to the current invention.

Anti-Drug Antibody Assay Using Human FcγRI-Detection and Drug Antibody Capture Via Biotinylated Drug Biotinylated bispecific effector function silent anti-ANG2/VEGF antibody was bound to streptavidin-coated microtiter plates (SA-MTP) in the first step. Excess of unbound antibody was removed by washing. Samples/standards, e.g. monoclonal anti-idiotypic anti-VEGF antibody antibody M-1.17.5, spiked in cynomolgus monkey serum was added to the wells of the SA-MTP coated with biotinylated anti-ANG2/VEGF antibody and incubated for 1 hour. After washing, the wells were incubated with digoxigenylated human Fcgamma receptor I (FcγRI, non-digoxigenylated FcγRI from R&D systems, Cat-No: 1257-FC). After washing the bound digoxigenylated human FcγRI was detected with a horseradish peroxidase (HRP) conjugated anti-digoxigenin antibody. After a further washing step, ABTS substrate was added. The signal was measured by ELISA reader at 405 nm wavelength (reference wavelength: 490 nm). Absorbance values of each serum sample were determined in duplicates. A scheme of the assay is depicted in FIG. 1.

| M-1.17.5 antibody concentration [ng/ml] | signal OD (405 nm) [AU] |
|---|---|
| 100 | 2.152 |
| 50 | 1.310 |
| 25 | 0.685 |
| 13 | 0.341 |
| 6 | 0.196 |
| 3 | 0.124 |
| 2 | 0.097 |
| 0 | 0.070 |

The drug tolerance of this assay was determined by spiking different concentrations of the bispecific anti-ANG2/VEGF antibody in a sample and determining the resulting extinction. The results are shown in the following table (columns: anti-ANG2/VEGF antibody concentration; rows: M-1.17.5 antibody concentration). To determine the cut-off 16 different single non-treated blank cynomolgus serum samples were measured on the same plate. The cut-off was calculated as follows: mean of single sera+two-times the standard deviation. The cut off was calculated as 0.1 AU for this plate

| [μg/mL] | | | | | | | | |
|---|---|---|---|---|---|---|---|---|
| 40 | 20 | 10 | 5 | 2.5 | 1.25 | 0.625 | 0 | [ng/mL] |
| 0.094 | 0.112 | 0.174 | 0.273 | 0.669 | 2.997 | 2.987 | 3.090 | 1500 |
| 0.075 | 0.077 | 0.109 | 0.174 | 0.303 | 0.736 | 2.695 | 3.006 | 750 |
| 0.071 | 0.065 | 0.078 | 0.105 | 0.171 | 0.317 | 0.962 | 2.939 | 375 |
| 0.074 | 0.056 | 0.064 | 0.076 | 0.111 | 0.173 | 0.395 | 2.769 | 188 |
| 0.063 | 0.054 | 0.057 | 0.064 | 0.081 | 0.116 | 0.209 | 2.277 | 94 |
| 0.064 | 0.049 | 0.053 | 0.058 | 0.063 | 0.084 | 0.119 | 1.470 | 47 |
| 0.060 | 0.048 | 0.049 | 0.054 | 0.057 | 0.066 | 0.083 | 0.782 | 23 |
| 0.062 | 0.049 | 0.055 | 0.051 | 0.050 | 0.051 | 0.049 | 0.053 | 0 |

EXAMPLE 2 (COMPARATIVE EXAMPLE)

Bridging Format Anti-Drug Antibody Assay

In a first step biotinylated anti-ANG2/VEGF antibody, positive control antibody (PC; mixture of the two anti-idiotypic antibodies against VEGF and ANG2 mAb<Id<Ang2>M2.6.81-IgG and mAb<Id<VEGF>M-2.45.51 (alternatively the polyclonal anti-idiotypic antibody against the anti-ANG2/VEGF antibody pAb<Id<Ang2/VEGF>>Rb-IgG could be used)) and sample, respectively, as well as first detection antibody (digoxigenylated anti-ANG2/VEGF antibody) were pre-incubated overnight at room temperature (RT) on a microtiter plate (MTP) shaker. In a second step pre-incubated PC and samples were transferred to a streptavidin coated MTP (SA-MTP). The excess of unbound antibody was removed by washing three times with 300 μL buffer each. After washing the complex-bound digoxigenylated anti-ANG2/VEGF antibody was detected with a horseradish peroxidase conjugated anti-digoxigenin antibody (incubation for 1 hour at room temperature, 500 rpm shaking). After a further washing step (three times 300 μL buffer) ABTS substrate was added. The signal was measured by ELISA reader at 405 nm wavelength (reference wavelength: 490 nm). Absorbance values of each serum sample were determined in triplicates. A scheme of the assay is depicted in FIG. 2.

| M-2.6.81/M-2.45.51 mixture antibody concentration [ng/ml] | signal OD (405 nm) [AU] |
|---|---|
| 400 | 2.033 |
| 200 | 1.797 |
| 100 | 1.299 |
| 50 | 0.810 |
| 25 | 0.474 |
| 12.5 | 0.290 |
| 6.25 | 0.176 |
| 0 | 0.073 |

The drug tolerance of this assay was determined by spiking different concentrations of the bispecific anti-ANG2/VEGF antibody in a sample and determining the resulting extinction. The results are shown in the following table (columns: anti-ANG2/VEGF antibody concentration; rows: PC antibody concentration). To determine the cut-off, 16 different single non-treated blank cynomolgus serum samples were measured on the same plate. The cut-off was calculated as follows: mean of single sera+two-times the standard deviation. The calculated cut off was 0.045 AU for this plate.

| [μg/mL] | | | | | | |
|---|---|---|---|---|---|---|
| 10 | 3 | 1 | 0.3 | 0.1 | 0 | [ng/mL] |
| 0.103 | 0.238 | 0.351 | 0.843 | 1.511 | 2.101 | 64 |
| 0.065 | 0.130 | 0.190 | 0.403 | 0.797 | 1.220 | 32 |
| 0.045 | 0.079 | 0.115 | 0.226 | 0.429 | 0.696 | 16 |
| 0.034 | 0.051 | 0.071 | 0.130 | 0.233 | 0.374 | 8 |
| 0.028 | 0.037 | 0.047 | 0.077 | 0.128 | 0.200 | 4 |
| 0.027 | 0.029 | 0.037 | 0.050 | 0.076 | 0.116 | 2 |
| 0.025 | 0.025 | 0.031 | 0.038 | 0.050 | 0.073 | 1 |
| 0.021 | 0.022 | 0.022 | 0.024 | 0.022 | 0.021 | 0 |

EXAMPLE 3

Measurement of Cynomolgus Study Samples—Comparison of the Anti-Drug Assay According to the Invention and Conventional Bridging Anti-Drug Antibody Assay Thirteen samples of different animals were diluted to a serum amount of 2% in low cross buffer (Candor Bioscience GmbH, Wangen, Germany) and subsequently subjected to the assay as described in Example 1. To determine the cut-off, 16 different single non-treated blank cynomolgus serum samples were measured on the same plate. The cut-off was calculated as follows: mean of single sera+two-times the standard deviation.

The results are depicted in FIG. 3. For eight of the thirteen samples the anti-drug antibody assay according to the current invention resulted in a readout of at least twice the cut-off. The remaining samples were determined to be negative (readout at most 50% of the cut-off).

The same thirteen samples were processed in the anti-drug antibody bridging assay as described in Example 2.

Figure 4:
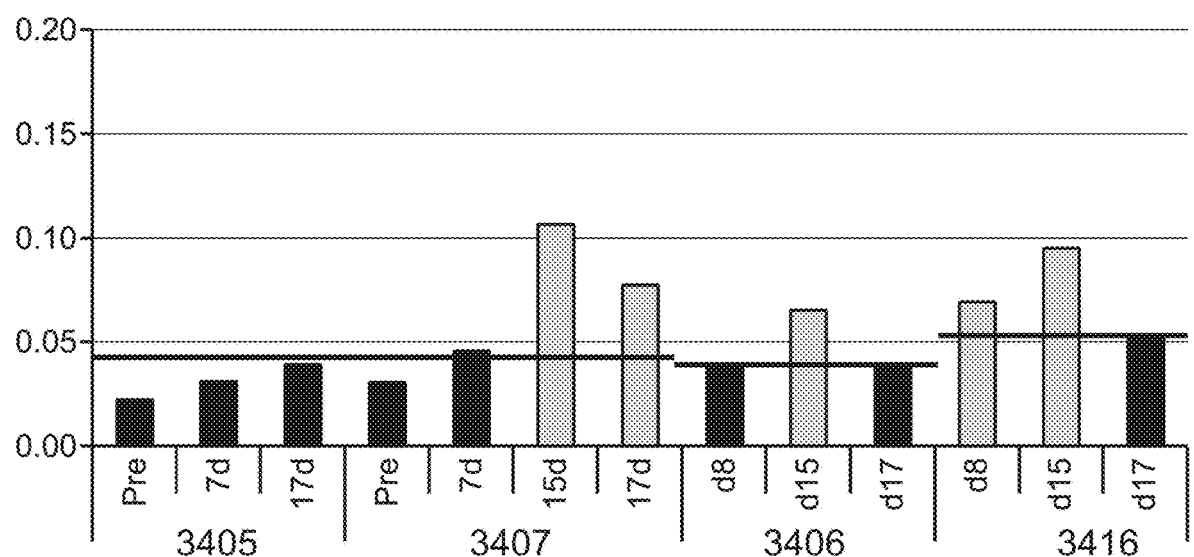
FIG. 4—Anti-drug antibody assay result of thirteen samples determined with a bridging anti-drug antibody assay.

The results are depicted in FIG. 4. For one of the thirteen samples the bridging anti-drug antibody assay resulted in a readout of about most twice the cut-off and for four of the thirteen samples the bridging anti-drug antibody assay resulted in a readout of between the cut-off and twice the cut-off. The remaining samples were determined to be negative (readout more than 50% of the cut-off).

EXAMPLE 4

Figure 5:
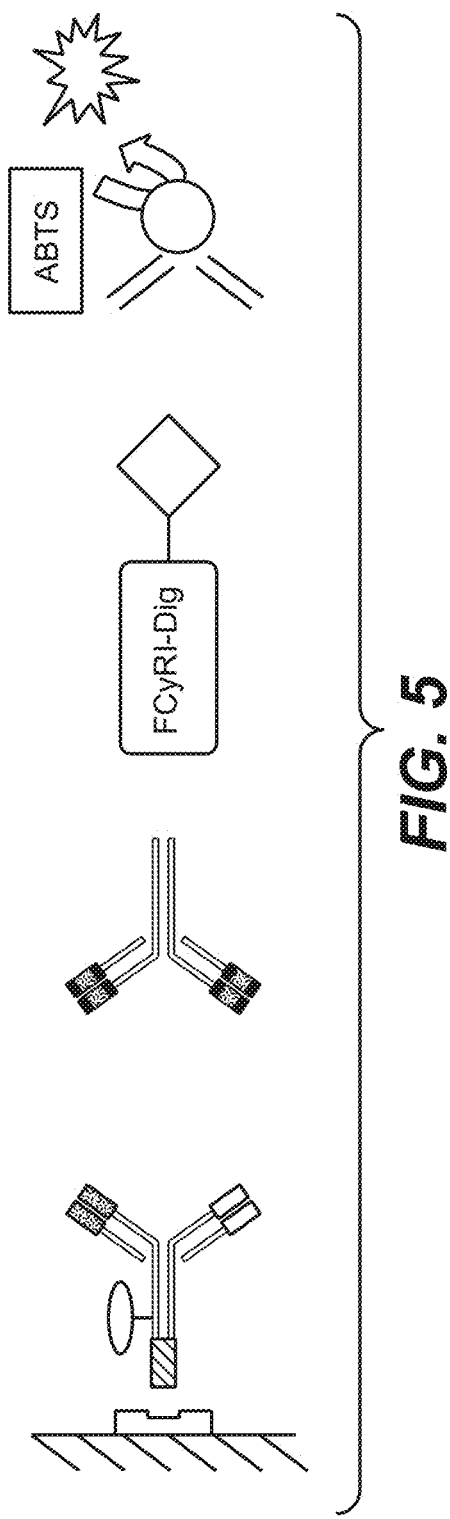
FIG. 5—Scheme of an anti-drug antibody assay using human FcγRI according to the invention.

Anti-Drug Antibody Assay with Human FcyRI-Detection and Drug Antibody Capture Via Biotinylated Drug Biotinylated effector silent anti-cyno CEA antibody (<Cyno-CEA>PGLALA) IL2 conjugate was immobilized on streptavidin-coated microtiter plates (SA-MTP) in the first step. Excess of unbound antibody was removed by washing. Samples/standards, e.g. polyclonal rabbit anti-idiotypic anti-CEA antibody antibody spiked in cynomolgus monkey serum, were added to wells of an SA-MTP coated with the biotinylated effector silent anti-cyno CEA antibody and incubated for one hour. After washing, the wells were incubated with digoxigenylated human FcyRI. After washing the complex-bound digoxigenylated human FcyRI was detected with a horseradish peroxidase conjugated anti-digoxigenin-antibody. After a further washing step ABTS substrate was added. The signal was measured by ELISA reader at 405 nm wavelength (reference wavelength: 490 nm). Absorbance values of each serum sample were determined in triplicates. A scheme of the assay is depicted in FIG. 5.

| anti-idiotypic anti-CEA antibody antibody concentration [ng/ml] | signal OD (405 nm) [AU] |
|---|---|
| 100 | 2.073 |
| 50 | 1.771 |
| 25 | 1.111 |
| 12.5 | 0.575 |
| 6.25 | 0.285 |
| 3.125 | 0.152 |
| 1.5625 | 0.102 |
| 0.0000 | 0.052 |

EXAMPLE 5

Measurement of Cynomolgus Study Samples—Comparison of the Anti-Drug Assay According to the Invention and Conventional Bridging Anti-Drug Antibody Assay Forty-two samples of different animals were diluted to a serum amount of 2% in low cross buffer (Candor Bioscience GmbH, Wangen, Germany) and subsequently subjected to the assay as described in Example 4. Samples were measured on tow plates. To determine the cut-off, 16 different single cynomolgus serum samples were measured on each plate. The plate-specific cut-off was calculated as follows: mean of single sera+two-times the standard deviation.

Figure 6:
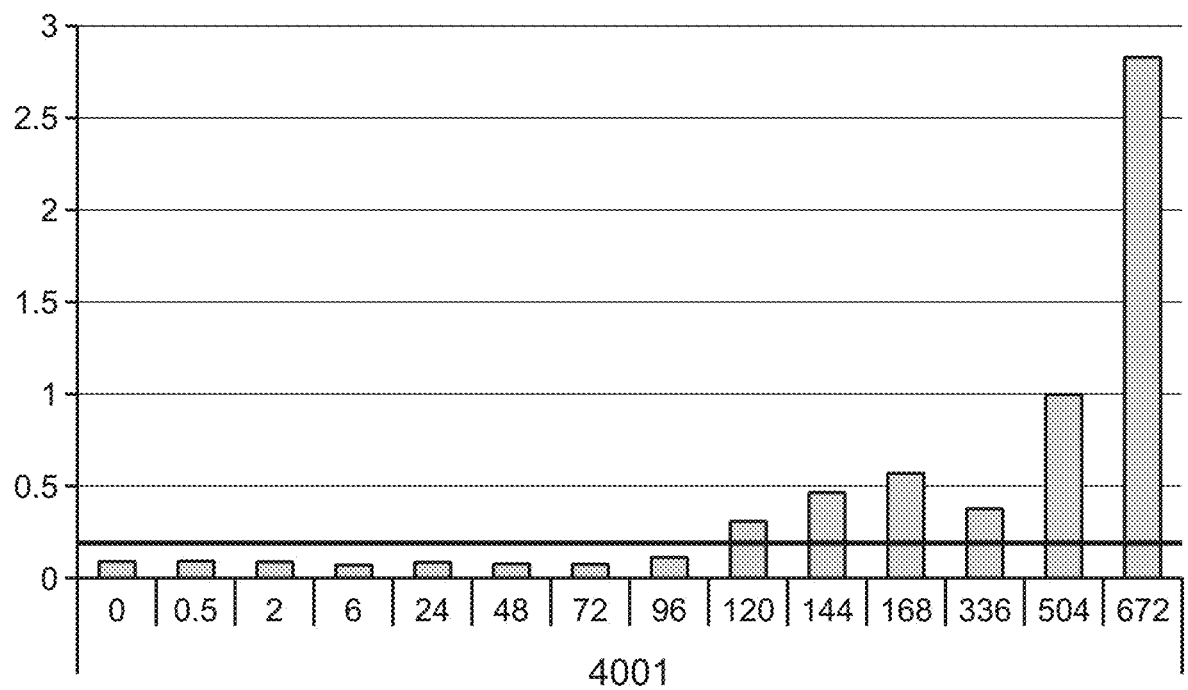
FIG. 6—Anti-drug antibody assay result of fourteen samples obtained from one experimental animal determined with the anti-drug antibody assay according to the current invention (x-axis: time after first dosing).

Exemplary results for fourteen samples from the same animal on the first plate are depicted in FIG. 6. For eight of the twenty-four samples of the first plate the anti-drug antibody assay according to the current invention resulted in a significantly positive readout well above the cut-off. The remaining samples were determined to be negative (readout significantly below the cut-off).

The same twenty samples were processed in the anti-drug antibody bridging assay as described in Example 2.

Figure 7:
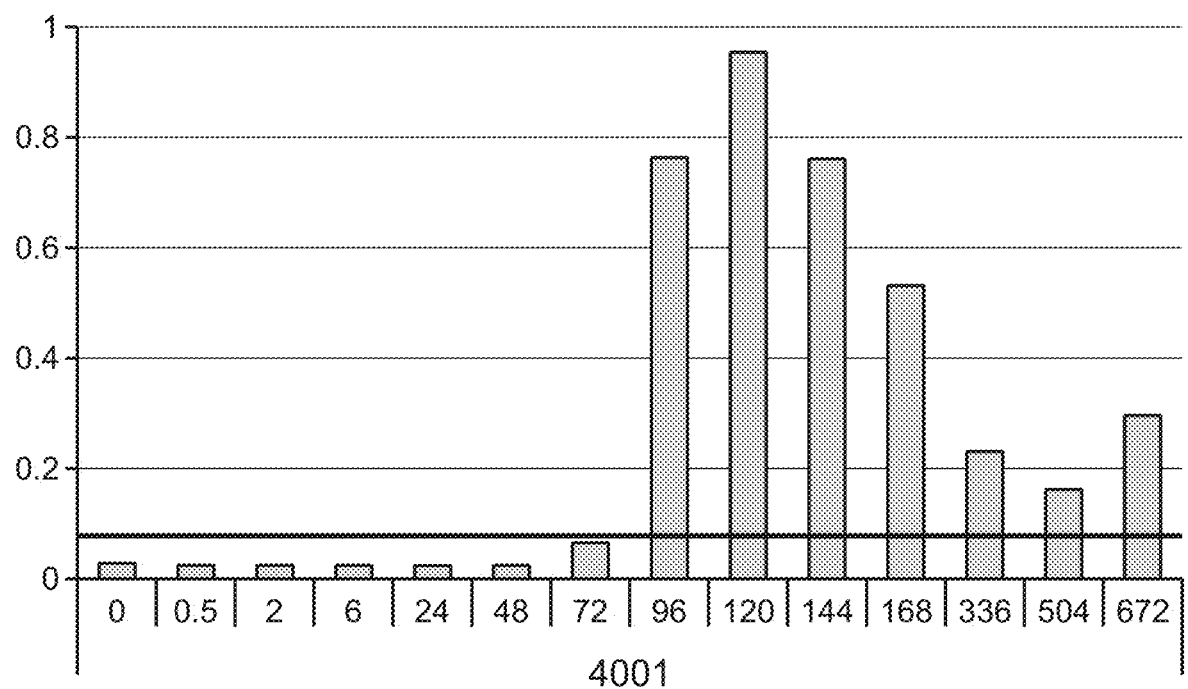
FIG. 7—Anti-drug antibody assay result of fourteen samples obtained from one experimental animal determined with a conventional bridging anti-drug antibody assay (x-axis: time after first dosing).

The results for the same fourteen samples as shown in FIG. 6 are depicted in FIG. 7. For twelve of the twenty samples the bridging anti-drug antibody assay resulted in a positive. The remaining samples were determined to be negative (readout below the cut-off).

The second plate included twenty-three samples of two animals. These samples were also analyzed in the bridging anti-drug antibody assay. For twelve of the twenty-three samples the anti-drug antibody assay according to the current invention resulted in a positive readout. The remaining samples were determined to be negative (readout below the cut-off). Measurement of these twenty-three samples in the bridging anti-drug antibody assay resulted in the same twelve positive samples.

Figure 8A:
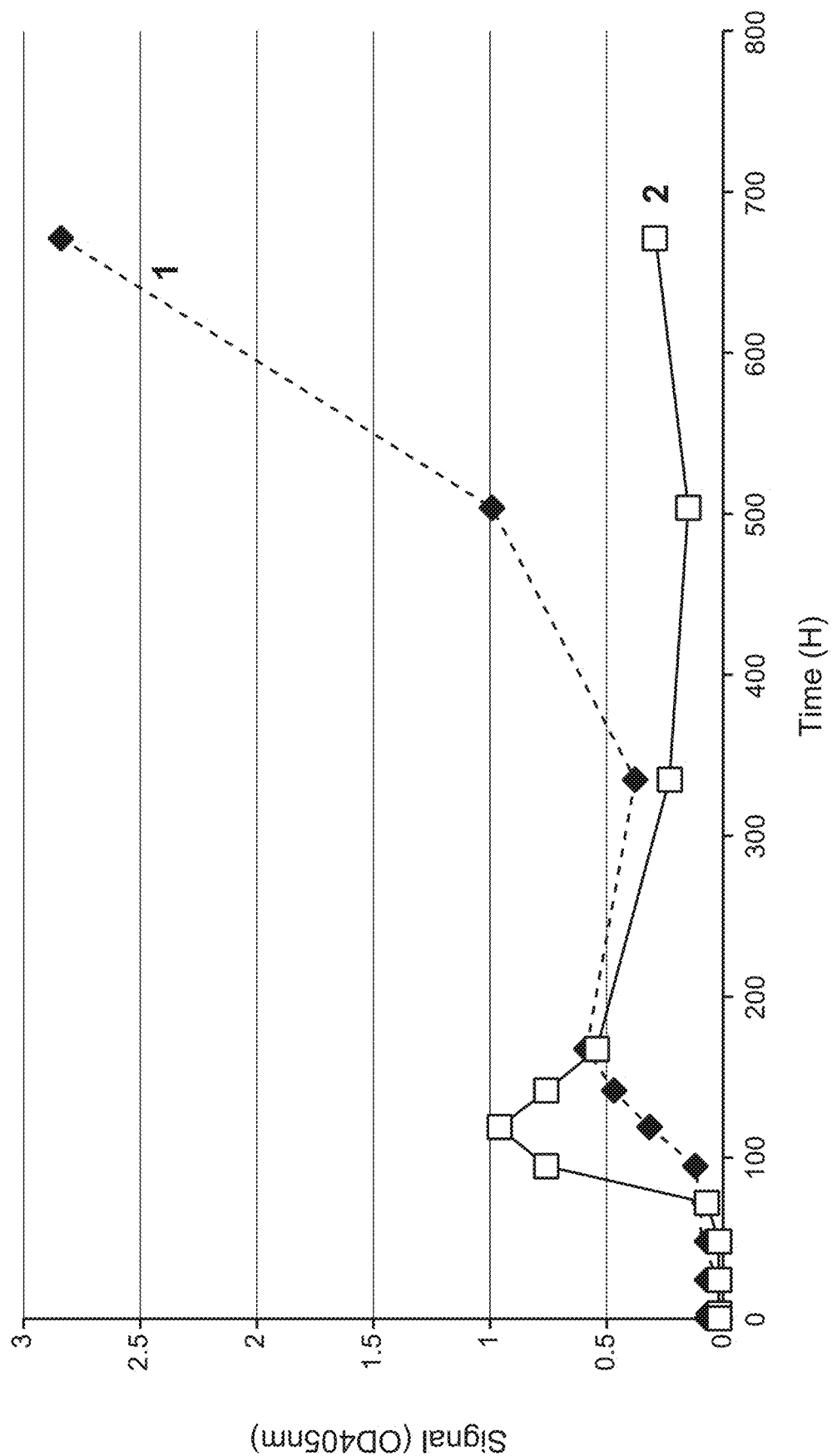
FIG. 8A: Animal 1.
Figure 8B:
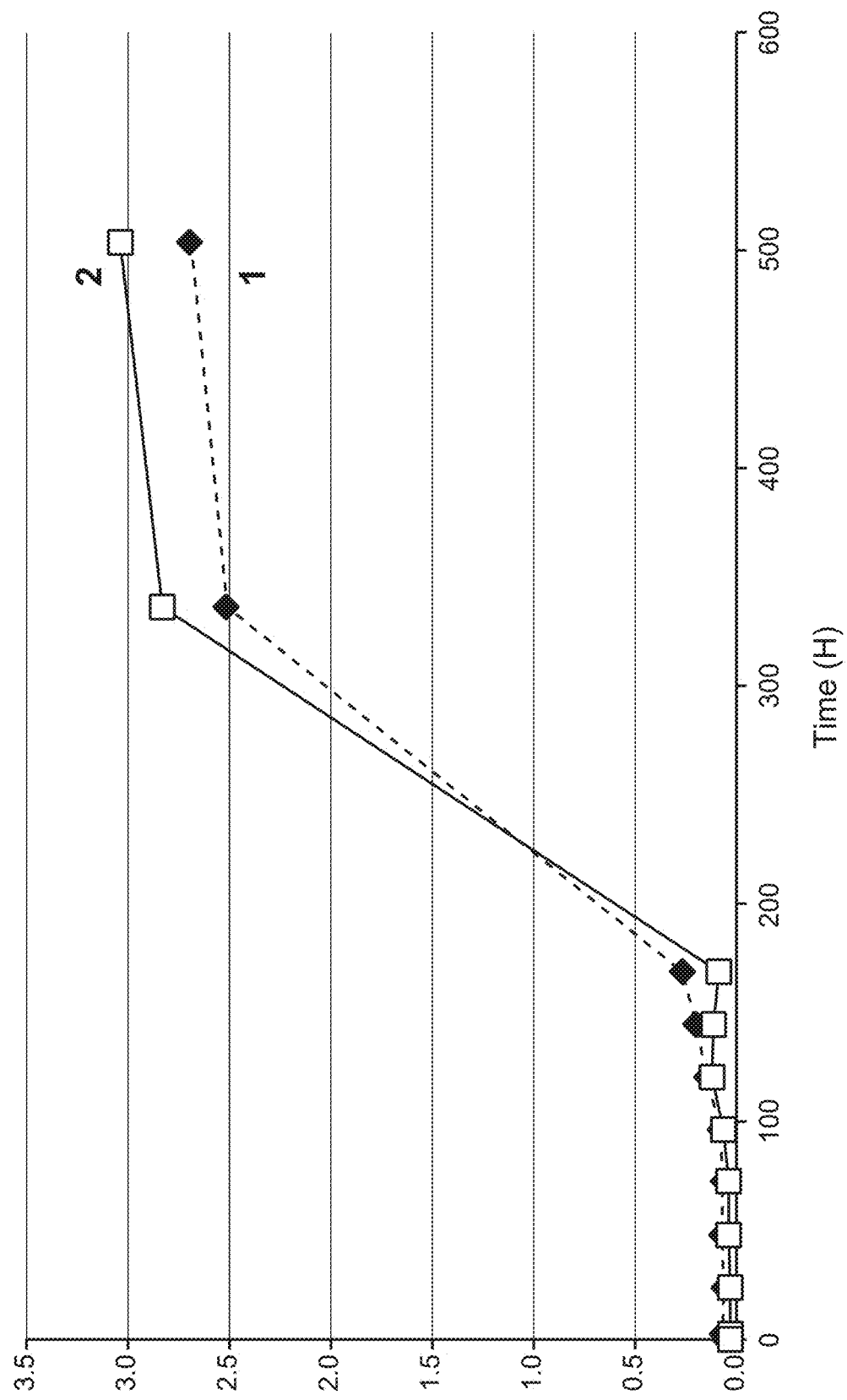
FIG. 8B: Animal 2.
Figure 8C:
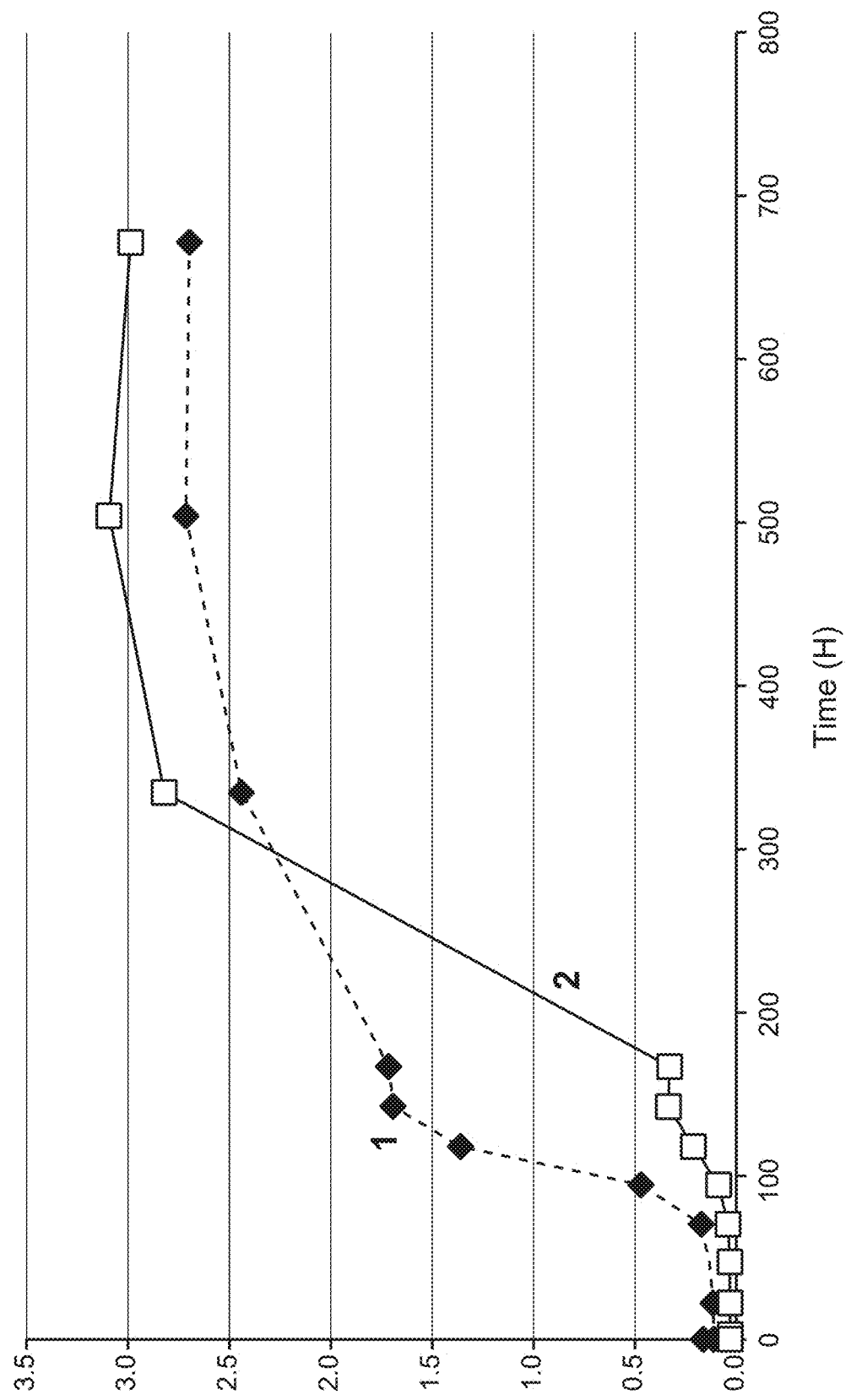
FIG. 8C: Animal 3.

Comparative results for three different animals obtained with the assay as reported herein and a conventional bridging assay are shown in FIGS. 8a to 8c reduced to the same scale.

For the first animal a starting sample and fourteen samples taken at different time points for up to four weeks after administration of the drug were analyzed using an assay according to the invention and a bridging anti-drug antibody assay.

It can be seen that with the bridging anti-drug antibody assay a response maximum was determined for the sample taken at about 100 h. With the anti-drug antibody assay according to the current invention a continuous increase in the readout can be seen.

For the second animal a starting sample and 10 samples, taken at different time points for up to three weeks after administration of the drug were analyzed using an assay according to the invention and a bridging anti-drug antibody assay. The results are shown in FIG. 8b. It can be seen that both assay show the same readout increase at about 200 h post dosing. No significant difference in readout between the two assays can be observed up to 504 h post dosing.

For the third animal a starting sample and 11 samples, taken at different time points for up to four weeks after administration of the drug were analyzed using an assay according to the invention and a bridging anti-drug antibody assay. The results are shown in FIG. 8c. It can be seen that both assay show the same readout increase at about 72 h post dosing. With the anti-drug antibody assay according to the current invention, this increase is much stronger though. A second increase can be observed for both assays at about 162 h post dosing, leading to about the same readouts for both assays.

EXAMPLE 6

Anti-Drug Antibody Assay with Human FcyRI-Detection and Drug Antibody Capture Via the Antigen Biotinylated VEGF was bound to streptavidin-coated microtiter plates (SA-MTP) in the first step. Excess of unbound antigen was removed by washing. In parallel, standards were prepared by pre-incubation of monoclonal anti-idiotypic anti-VEGF antibody antibody M-1.17.5 in a dilution series with monoclonal anti-Ang2/VEGF antibody spiked in cynomolgus monkey serum. All samples were prepared twice. Samples were diluted 1:50 i) in low cross buffer and ii) in low cross buffer containing 1 µg/mL monoclonal anti-Ang2/VEGF antibody. Standards and samples were added to wells of the VEGF-coated SA-MTP and incubated for 1 hour. After washing, the wells were incubated with digoxigenylated human FcyRI. After washing the complex-bound digoxigenylated human FcyRI was detected with a horseradish peroxidase (HRP) conjugated anti-digoxigenin antibody. After a further washing step, the HRP substrate ABTS was added. The signal was measured by ELISA reader at 405 nm wavelength (reference wavelength: 490 nm). Absorbance values of each serum sample were determined in triplicates. A scheme of the assay is depicted in FIG. 9.

| M-1.17.5 antibody concentration [ng/ml] | signal (OD 405 nm) [AU] |
|---|---|
| 100 | 0.293 |
| 50 | 0.200 |
| 25 | 0.163 |
| 12.5 | 0.143 |
| 6.25 | 0.128 |
| 3.125 | 0.122 |
| 1.5625 | 0.123 |
| 0 | 0.130 |

EXAMPLE 7

Anti-Drug Antibody Assay with Human FcyRI-Detection and Drug Antibody Capture Via an Anti-Idiotypic Antibody Biotinylated monoclonal anti-idiotypic anti-VEGF antibody antibody was bound to the wells of a streptavidin-coated microtiter plate (SA-MTP) in the first step. Excess of unbound antibody was removed by washing. Standards were prepared by pre-incubation of monoclonal anti-idiotypic anti-VEGF antibody M-1.17.5 in a dilution series with monoclonal anti-Ang2/VEGF antibody spiked in cynomolgus monkey serum. All samples were prepared twice. Samples were diluted 1:50 i) in low cross buffer and ii) in low cross buffer containing 1 µg/mL monoclonal anti-Ang2/VEGF antibody. Standards and samples were added to the wells of the VEGF-coated SA-MTP and incubated for 1 hour. After washing, the wells were incubated with digoxigenylated human FcyRI. After washing the complex-bound digoxigenylated human FcyRI was detected with a horseradish peroxidase (HRP) conjugated anti-digoxigenin antibody. After a further washing step, the HRP of the antibody-enzyme conjugates catalyzes the color reaction of ABTS substrate. The signal was measured by ELISA reader at 405 nm wavelength (reference wavelength: 490 nm). Absorbance values of each serum sample were determined in triplicates. A scheme of the assay is depicted in FIG. 10.

| M-1.17.5 antibody concentration [ng/ml] | signal (OD 405 nm) [AU] |
|---|---|
| 25.00 | 2.326 |
| 12.50 | 1.257 |
| 6.25 | 0.626 |
| 3.13 | 0.322 |
| 1.56 | 0.191 |
| 0.78 | 0.124 |
| 0.39 | 0.091 |
| 0.20 | 0.069 |
| 0.10 | 0.063 |
| 0 | 0.056 |

EXAMPLE 8

Drug Tolerance of the Anti-Drug Antibody Assay with Human FcγRI-Detection and Drug Antibody Capture Via an Anti-Idiotypic Antibody The drug tolerance of this assay was determined by spiking different concentrations of the bispecific anti-ANG2/VEGF antibody in a sample and determining the resulting extinction. The results are shown in the following table (columns: anti-ANG2/VEGF antibody concentration; rows: M-1.17.5 antibody concentration). To determine the cut-off, 16 different single non-treated blank cynomolgus serum samples were measured on the same plate. The cut-off was calculated as follows: mean of single sera+two-times the standard deviation. The calculated cut off was 0.13 AU for this plate.

| [µg/mL] | | | | | | | | |
|---|---|---|---|---|---|---|---|---|
| 40 | 20 | 10 | 5 | 2.5 | 1.25 | 0.625 | 0 | [ng/mL] |
| 0.911 | 1.797 | 2.773 | 3.017 | 2.568 | 2.641 | 2.541 | 0.056 | 1500 |
| 0.422 | 0.899 | 1.797 | 2.724 | 2.334 | 2.544 | 2.567 | 0.066 | 750 |
| 0.213 | 0.422 | 0.882 | 1.741 | 1.811 | 2.254 | 2.435 | 0.054 | 375 |
| 0.120 | 0.198 | 0.411 | 0.814 | 1.087 | 1.621 | 2.04 | 0.056 | 188 |
| 0.083 | 0.124 | 0.205 | 0.380 | 0.582 | 0.943 | 1.387 | 0.064 | 94 |
| 0.064 | 0.082 | 0.115 | 0.187 | 0.286 | 0.481 | 0.716 | 0.068 | 47 |
| 0.059 | 0.066 | 0.082 | 0.115 | 0.174 | 0.264 | 0.373 | 0.083 | 23 |
| 0.05 | 0.05 | 0.05 | 0.049 | 0.085 | 0.093 | 0.089 | 0.095 | 0 |

EXAMPLE 9

Figure 11:
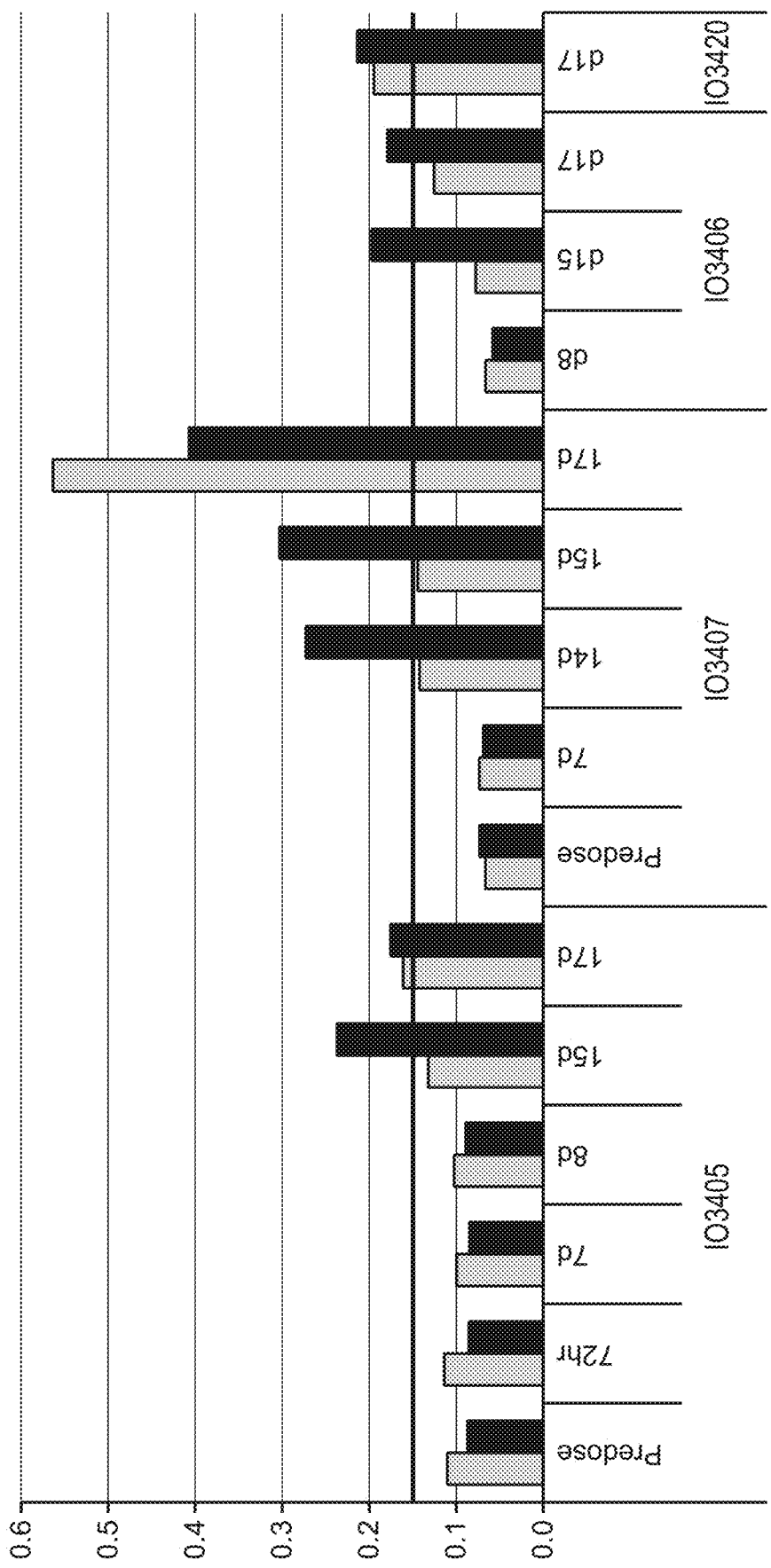
FIG. 11—Anti-drug antibody assay result of fifteen samples determined with the anti-drug antibody assay according to the current invention; left column: without added drug, right column: with added drug (1 μg/mL).

Measurement of Cynomolgus Study Samples—Determination of Anti-Drug Antibody with an Assay According to the Invention in the Presence and Absence of Drug Fifteen samples of different animals were diluted to a serum amount of 2% in low cross buffer (Candor Bioscience GmbH, Wangen, Germany). From each dilution each two samples were prepared. The first sample was subjected to the assay as described in Example 7, the second sample was spiked with 1 µg/mL monoclonal anti-Ang2/VEGF antibody and thereafter subjected to the assay as described in Example 7. To determine the cut-off, 16 different single cynomolgus serum samples were measured on the same plate. The cut-off was calculated as follows: mean of single sera+two-times the standard deviation. The results are depicted in FIG. 11.

EXAMPLE 10

Figure 12:
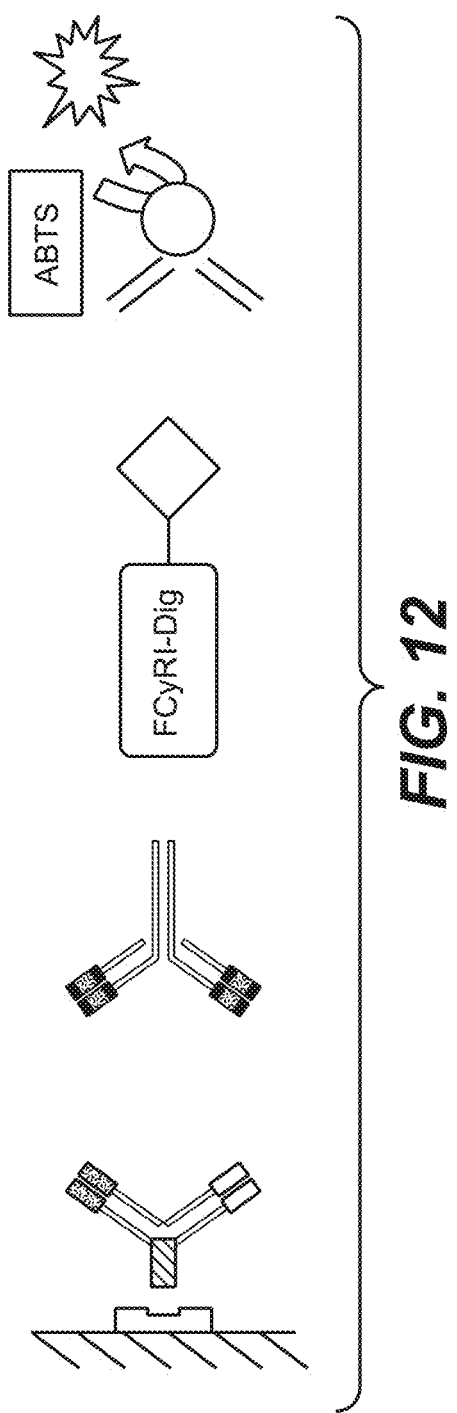
FIG. 12—Anti-drug antibody assay using human FcγRI according to the invention.
Figure 13:
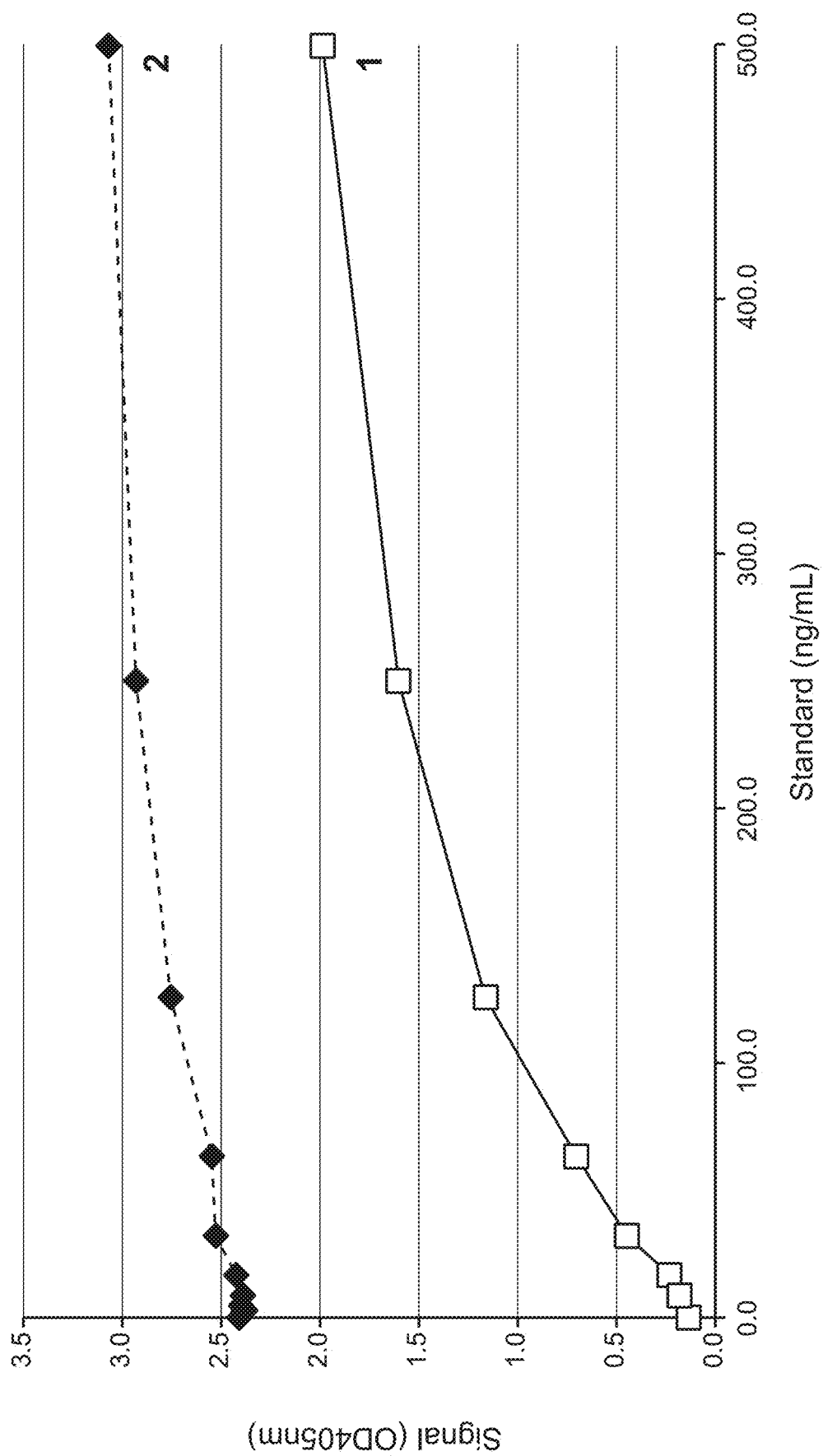
FIG. 13—Comparison of the results obtained with an assay according to Example 1 (1) and an assay according to Example 10 (2).

Anti-Drug Antibody Assay Using Human FcγRI-Detection and Drug Antibody Capture Via Biotinylated F(ab')$_2$ Fragment of the Drug Biotinylated bispecific F(ab')$_2$ fragment of anti-ANG2/VEGF antibody was bound to streptavidin-coated microtiter plates (SA-MTP) in the first step. Excess of unbound antibody was removed by washing. Samples/standards, e.g. monoclonal anti-idiotypic anti-VEGF antibody antibody M-1.17.5, spiked in 10% human pool serum was added to the wells of an SA-MTP coated with biotinylated anti-ANG2/VEGF antibody F(ab')$_2$ fragment and incubated for one hour. After washing, the wells were incubated with digoxigenylated human FcγRI. After washing the bound digoxigenylated human FcγRI was detected with a horse-radish peroxidase (HRP) conjugated anti-digoxigenin antibody. After a further washing step, ABTS substrate was added. The signal was measured by ELISA reader at 405 nm wavelength (reference wavelength: 490 nm). Absorbance values of each serum sample were determined in duplicates. A scheme of the assay is depicted in FIG. 12. FIG. 13 shows assay results compared to the same samples measured as described in Example 1.

EXAMPLE 11

Determination of Interference of Oligomeric Target for ADA Assay with FcγRI-Detection and Drug Capture Via Biotinylated Drug The assay as described in Example 1, 2 and 7 was tested for interference of oligomeric target VEGF and ANG2. Targets were diluted from 100 ng/mL to 0.048 ng/mL in 100% cynomolgus pool plasma and tested in the assay. Results are shown in the Tables below.

| VEGF [ng/ml] | Assay according to Example 2 bridging ADA [OD 405 nm] | Assay according to Example 1 (capture via drug) [OD 405 nm] | Assay according to Example 7 (capture via anti-idiotypic antibody) [OD 405 nm] |
|---|---|---|---|
| 100 ng/mL | 2.829 | 0.051 | 0.089 |
| 50 ng/mL | 2.338 | 0.048 | 0.090 |
| 25 ng/mL | 1.693 | 0.049 | 0.090 |
| 12.5 ng/mL | 0.921 | 0.049 | 0.093 |
| 6.25 ng/mL | 0.510 | 0.051 | 0.094 |
| 3.13 ng/mL | 0.274 | 0.052 | 0.092 |
| 1.56 ng/mL | 0.138 | 0.051 | 0.093 |
| 0.781 ng/mL | 0.083 | 0.050 | 0.088 |
| 0.391 ng/mL | 0.058 | 0.049 | 0.092 |
| 0.195 ng/mL | 0.039 | 0.047 | 0.093 |
| 0.0977 ng/mL | 0.033 | 0.053 | 0.090 |
| 0.0489 ng/mL | 0.025 | 0.049 | 0.090 |
| Cut Off | 0.05 | 0.059 | 0.108 |

| ANG2 [ng/ml] | Assay according to Example 2 bridging ADA [OD 405 nm] | Assay according to Example 1 (capture via drug) [OD 405 nm] | Assay according to Example 7 (capture via anti-idiotypic antibody) [OD 405 nm] |
|---|---|---|---|
| 100 ng/mL | 0.140 | 0.076 | 0.087 |
| 50 ng/mL | 0.076 | 0.064 | 0.090 |
| 25 ng/mL | 0.052 | 0.057 | 0.089 |
| 12.5 ng/mL | 0.038 | 0.052 | 0.089 |
| 6.25 ng/mL | 0.031 | 0.050 | 0.089 |
| 3.13 ng/mL | 0.028 | 0.054 | 0.092 |
| 1.56 ng/mL | 0.024 | 0.054 | 0.097 |
| 0.781 ng/mL | 0.024 | 0.050 | 0.099 |
| 0.391 ng/mL | 0.022 | 0.050 | 0.097 |
| 0.195 ng/mL | 0.024 | 0.050 | 0.092 |
| 0.0977 ng/mL | 0.022 | 0.052 | 0.092 |
| 0.0489 ng/mL | 0.022 | 0.050 | 0.091 |
| Cut Off | 0.05 | 0.059 | 0.108 |

EXAMPLE 12

Assessment of Binding/Specificity of huFcγRI by Surface Plasmon Resonance

All measurements were performed with the BIAcore® T100 instrument using a SA-CAP-chip. Unless otherwise indicated, all incubations were performed in HBS-buffer (HEPES, NaCl, pH 7.4) at 25° C. The Chip was coated with a saturating amount of streptavidin in the first step by injection of SA-CAP reagent for 300 sec. at 2 µl/min. Coating of the chip with biotinylated human Fcgamma receptor I (huFcyRI) was achieved by injection of a solution comprising 10 µg/mL huFcyRI-Bi for 60 sec. at 10 µL/min. Subsequently, the different samples were injected for 60 sec. at a flow rate of 30 µL/min. Signals were measured after injection. To eliminate unspecific binding, a reference flow cell was used to measure the same samples without immobilized huFcyRI. Signals of reference flow cell were subtracted from the signals of the measurement flow cell. All animal sera were diluted 1:100 in HBS-P buffer. Purified proteins were diluted to a concentration of 10 µg/mL each. Using BIAevaluation Software from BIAcore® the reference subtracted response signals after end of injection were calculated.

| sample | signal (RU) |
|---|---|
| buffer (blank) | 0 |
| serum (1%) | |
| cynomolgus | 38.1 |
| human | 45.2 |
| mouse | 38.7 |
| baboon | 45.4 |
| chimpanzee | 86.4 |
| dog | 33.1 |
| rat | −0.8 |
| guinea pig | 4 |
| rhesus monkey | 58.8 |
| rabbit | 49.1 |
| minipig | −20 |
| purified antibodies | |
| human IgG1 | 138.7 |
| human IgG4 | 20.2 |
| human IgG4 with S228P L235E mutations | 2.6 |
| human IgM | 5.2 |
| human IgG1 with L234A L235A mutations | 4 |
| human IgG1 with P329G L243A L235A mutations | 1.5 |
| human IgG1 P329G L234A L235A I253A H310A H434A mutations | 1.8 |
| mouse IgG2a | 31.1 |
| mouse IgG1 | 3 |

What is claimed is:

1. An anti-drug antibody immunoassay for the determination of the presence of an anti-drug antibody against an effector function suppressed human or humanized drug antibody in a sample comprising the following steps in the following order:
   a. Incubating a sample comprising mammalian blood serum with full length human Fcgamma receptor I or an Fc-binding region of full-length human Fcgamma I so that a complex between the anti-drug antibody against the effector function suppressed human or humanized drug antibody present in the sample and the human Fcgamma receptor I or the Fc-binding region of full-length human Fcgamma I forms, whereby the full length human Fcgamma receptor I or the Fc-binding region of full-length human Fcgamma I is conjugated to a detectable label;
   b. isolating the complex formed between the anti-drug antibody against the effector function suppressed human or humanizued drug antibody and the human Fcgamma receptor I or the Fc-binding region of full-length human Fcgamma I; and
   c. determining the complex by the detectable label.

2. An anti-drug antibody immunoassay for the determination of the presence of an anti-drug antibody (ADA) against an effector function suppressed human or humanized drug antibody (EFS-DA) in a sample comprising the following steps in the following order:

a. incubating a solid phase on which the effector function suppressed human or humanized drug antibody has been immobilized with a sample comprising mammalian blood serum so that a solid-phase-bound drug antibody-anti-drug antibody complex is formed;
b. incubating the solid phase to which the drug antibody-anti-drug antibody complex formed in step a. is bound with full length human Fcgamma receptor I or an Fc-binding region of full-length human Fcgamma I, whereby the full length human Fcgamma receptor I or the Fc-binding region of full-length human Fcgamma I is conjugated to a detectable label; and
c. determining the formation of a solid-phase-bound complex in step b. by determining the presence of the detectable label; and
d. wherein determining the presence of the detectable label in step c. indicates the presence of an antidrug antibody against an effector function suppressed human or humanized drug antibody in the sample.

3. An anti-drug antibody immunoassay for the determination of the presence of an anti-drug antibody (ADA) against an effector function suppressed human or humanized drug antibody (EFS-DA) in a sample comprising the following steps in the following order:
a. incubating a solid phase on which the FAB (Fragment-Antigen Binding) of an effector function suppressed human or humanized drug antibody has been immobilized with a sample comprising mammalian blood serum so that a solid-phase-bound FAB-anti-drug antibody complex is formed;
b. incubating the solid phase (to which the FAB-anti-drug antibody complex formed in step a. is bound) with full length human Fcgamma receptor I or an Fc-binding region of full-length human Fcgamma I, whereby the full length human Fcgamma receptor I or the Fc-binding region of full-length human Fcgamma I is conjugated to a detectable label; and
c. determining the formation of a solid-phase bound complex in step b. by determining the presence of the detectable label and thereby determining the presence of an antidrug antibody against an effector function suppressed human.

4. An anti-drug antibody immunoassay for the determination of the presence of an anti-drug antibody (ADA) against an effector function suppressed human or humanized drug antibody (EFS-DA) in a sample comprising the following steps in the following order:
a. adding (excess) drug antibody to the sample (to transfer (any) anti-drug antibody present in the sample in a drug-antibody-anti-drug antibody complex), wherein the sample comprises mammalian blood serum;
b. incubating a solid phase on which the antigen to which the EFS-DA specifically binds has been immobilized with the sample obtained in step a. (so that a solid-phase-bound antigen-drug antibody-anti-drug antibody complex is formed),
c. incubating the solid phase (to which the antigen-drug antibody-anti-drug antibody complex formed in step b. is bound) with full length human Fcgamma receptor I or an Fc-binding region of full-length human Fcgamma I, whereby the full length human Fcgamma receptor I or the Fc-binding region of full-length human Fcgamma I is conjugated to a detectable label; and
d. determining the formation of a solid-phase-bound complex in step c. by determining the presence of the detectable label and thereby determining the presence of an antidrug antibody against an effector function suppressed human or humanized drug antibody in the sample.

5. An anti-drug antibody immunoassay for the determination of the presence of an anti-drug antibody (ADA) against an effector function suppressed human or humanized drug antibody (EFS-DA) in a sample comprising the following steps in the following order:
a. adding (excess) drug antibody to the sample (to transfer (any) anti-drug antibody present in the sample in a drug-antibody-anti-drug antibody complex), wherein the sample comprises mammalian blood serum;
b. incubating a solid phase on which full length human Fcgamma receptor I or an Fc-binding region of full-length human Fcgamma I has been immobilized with the sample obtained in step a. (so that a solid-phase-bound receptor-drug antibody-anti-drug antibody complex is formed);
c. incubating the solid phase (to which the receptor-drug antibody-anti-drug antibody complex formed in step b) is bound) with the antigen of the drug antibody, whereby the antigen is conjugated to a detectable label; and
d. determining the formation of a solid-phase-bound complex in step c. by determining the presence of the detectable label and thereby determining the presence of an antidrug antibody against an effector function suppressed human or humanized drug antibody in the sample.

6. An anti-drug antibody immunoassay for the determination of the presence of an anti-drug antibody (ADA) against an effector function suppressed human or humanized drug antibody (EFS-DA) in a sample comprising the following steps in the following order:
a. adding (excess) drug antibody to the sample (to transfer (any) anti-drug antibody present in the sample in a drug-antibody-anti-drug antibody complex), wherein the sample comprises mammalian blood serum;
b. incubating a solid phase on which an anti-drug antibody against the drug antibody has been immobilized with the sample obtained in step a. (so that a solid-phase-bound anti-drug antibody-drug antibody-anti-drug antibody complex is formed);
c. incubating the solid phase (to which the anti-drug antibody-drug antibody-anti-drug antibody complex formed in step b. is bound) with full length human Fcgamma receptor I or an Fc-binding region of full-length human Fcgamma I, whereby the full length human Fcgamma receptor I or the Fc-binding region of full-length human Fcgamma I is conjugated to a detectable label; and
d. determining the formation of a solid-phase-bound complex in step c. by determining the presence of the detectable label and thereby determining the presence of an anti-drug antibody against an effector function suppressed human or humanized drug antibody in the sample.

7. The immunoassay according to claim 2, wherein each incubating step is followed by washing the solid phase to remove unbound compounds.

8. The immunoassay according to claim 2, wherein the assay is for the determination of the presence and the amount of an anti-drug antibody (ADA) against an effector function suppressed human or humanized drug antibody (EFS-DA) in a sample and comprises the further steps: determining the formation of a solid-phase-bound complex in the previous step by determining the presence of the detectable label and determining the amount of an anti-drug antibody against an effector function suppressed human or humanized drug antibody in the sample by correlating the amount of the determined label with the amount of the anti-drug antibody using a standard curve.

9. The immunoassay according to claim 2, wherein the effector function suppressed human or humanized drug antibody is an Immunoglobulin G (IgG) of the human subclass IgG1 or IgG4.

10. The immunoassay according to claim 2, wherein the effector function suppressed human or humanized drug antibody is of the human subclass IgG1 and has the mutations L234A, L235A and P329G in both Fc-region polypeptides or wherein the effector function suppressed human or humanized drug antibody is of the human subclass IgG4 and has the mutations S228P, L235E and P329G in both Fc-region polypeptides (numbering according to the EU numbering system according to Kabat).

11. The immunoassay according to claim 2, wherein the effector function suppressed human or humanized drug antibody is a bi specific antibody.

12. The immunoassay according to claim 2, wherein the effector function suppressed human or humanized drug antibody does not induce antibody-dependent cell-mediated cytotoxicity (ADCC).

13. The immunoassay according to claim 2, wherein the mammalian blood serum is human blood serum or cynomolgus blood serum.

14. The immunoassay according to claim 2, wherein the mammalian blood serum has been obtained from a mammal to which the effector function suppressed human or humanized drug antibody had been administered for the first time at least 2 days prior to obtaining the sample.

15. The immunoassay according to claim 2, wherein the sample comprises of from 0.5% (v/v) to 8% (v/v) mammalian serum, preferably about 2% (v/v) mammalian serum.

16. The immunoassay according to claim 2, wherein the anti-drug antibody against an effector function suppressed human or humanized drug antibody is of the IgG class.

17. The immunoassay according to claim 2, wherein the presence and/or amount of the label is determined using an enzyme linked color reaction, surface plasmon resonance, electrochemiluminescence, or radioimmunoassay.

18. The immunoassay according to claim 2, wherein the complex is a monomeric complex.

19. The immunoassay according to claim 2, wherein the complex is a 1:1 or a 1:1:1 complex.

* * * * *